(12) United States Patent
Reubelt et al.

(10) Patent No.: US 9,433,507 B2
(45) Date of Patent: Sep. 6, 2016

(54) NON-SPHERICAL ARTICULATING SURFACES IN SHOULDER AND HIP REPLACEMENT

(75) Inventors: Leo M. Reubelt, Hawthorne, NJ (US); Peter L. Verrillo, Wood Ridge, NJ (US)

(73) Assignee: Tornier, Inc., Bloomington, MN (US)

( * ) Notice: Subject to any disclaimer, the term of this patent is extended or adjusted under 35 U.S.C. 154(b) by 1929 days.

(21) Appl. No.: 11/689,445

(22) Filed: Mar. 21, 2007

(65) Prior Publication Data

US 2007/0225818 A1 Sep. 27, 2007

Related U.S. Application Data

(60) Provisional application No. 60/784,238, filed on Mar. 21, 2006.

(51) Int. Cl.
*A61F 2/32* (2006.01)
*A61F 2/40* (2006.01)
(Continued)

(52) U.S. Cl.
CPC . *A61F 2/32* (2013.01); *A61F 2/40* (2013.01); *A61F 2/4081* (2013.01); *A61F 2002/30253* (2013.01); *A61F 2002/30327* (2013.01); *A61F 2002/30332* (2013.01); *A61F 2002/30934* (2013.01); *A61F 2002/30945* (2013.01); *A61F 2002/3429* (2013.01); *A61F 2002/3496* (2013.01); *A61F 2002/365* (2013.01); *A61F 2002/3611* (2013.01); *A61F 2002/3623* (2013.01); *A61F 2002/3625* (2013.01); *A61F 2002/4018* (2013.01); *A61F 2002/4085* (2013.01); *A61F 2220/0033* (2013.01);

(Continued)

(58) Field of Classification Search
CPC .......................................................... A61F 2/32
USPC ....................................................... 623/19.13
See application file for complete search history.

(56) References Cited

U.S. PATENT DOCUMENTS 3,506,982 A * 4/1970 Steffee ........................ 623/21.16
3,694,820 A 10/1972 Scales et al.
(Continued)

FOREIGN PATENT DOCUMENTS

CH 426096 12/1966
CH 507704 5/1971
(Continued)

OTHER PUBLICATIONS

"Anatomic Glenoid, Surgical Technique," Smith & Nephew, 2000.
(Continued)

*Primary Examiner* — Bruce E Snow
*Assistant Examiner* — Melissa Hoban
(74) *Attorney, Agent, or Firm* — Knobbe Martens Olson & Bear LLP

(57) ABSTRACT

An orthopedic device and method of use are provided that incorporate complex, non-spherical articulating surfaces to allow a greater available range of motion compared with existing artificial shoulder joint and artificial hip joints. According to some embodiments, complex, non-spherical articulating surfaces can be incorporated on a humeral head and/or glenoid of a shoulder prosthesis. In other embodiments, complex, non-spherical articulating surfaces can be incorporated on the acetabulum and/or femoral head of a hip prosthesis. These non-spherical surfaces can be used to adjust constraint, joint thickness, soft tissue tension, moment and arc of motion, and in doing so, influence motion.

21 Claims, 23 Drawing Sheets

(51) Int. Cl.
  *A61F 2/30* (2006.01)
  *A61F 2/34* (2006.01)
  *A61F 2/36* (2006.01)
(52) U.S. Cl.
  CPC  *A61F2230/0076* (2013.01); *A61F 2250/0039* (2013.01)

(56) References Cited

U.S. PATENT DOCUMENTS

| | | |
|---|---|---|
| 3,815,157 A | 6/1974 | Skorecki et al. |
| 3,842,442 A | 10/1974 | Kolbel |
| 3,864,758 A | 2/1975 | Yakich |
| 3,869,730 A | 3/1975 | Skobel |
| 3,916,451 A | 11/1975 | Buechel et al. |
| 3,978,528 A | 9/1976 | Crep |
| 3,979,778 A | 9/1976 | Stroot |
| 3,992,726 A | 11/1976 | Freeman et al. |
| 4,003,095 A | 1/1977 | Gristina |
| 4,030,143 A | 6/1977 | Elloy et al. |
| 4,040,131 A | 8/1977 | Gristina |
| 4,054,955 A | 10/1977 | Seppo |
| 4,135,517 A | 1/1979 | Reale |
| 4,179,758 A | 12/1979 | Gristina |
| 4,206,517 A | 6/1980 | Pappas et al. |
| 4,261,062 A | 4/1981 | Amstutz et al. |
| 4,550,450 A | 11/1985 | Kinnett |
| 4,693,723 A | 9/1987 | Gabard |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazzeri et al. |
| 5,032,132 A | 7/1991 | Matsen, III et al. |
| 5,037,440 A * | 8/1991 | Koenig .................. 623/21.19 |
| 5,080,673 A | 1/1992 | Burkhead et al. |
| 5,080,685 A | 1/1992 | Bolesky et al. |
| 5,127,920 A | 7/1992 | MacArthur |
| 5,135,529 A | 8/1992 | Paxson et al. |
| 5,163,961 A | 11/1992 | Harwin |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,261,914 A | 11/1993 | Warren |
| 5,314,479 A | 5/1994 | Rockwood, Jr. et al. |
| 5,314,487 A | 5/1994 | Schryver et al. |
| 5,330,531 A | 7/1994 | Capanna |
| 5,358,526 A | 10/1994 | Tornier |
| 5,383,936 A | 1/1995 | Kubein-Meesenburg et al. |
| 5,425,779 A | 6/1995 | Schlosser et al. |
| 5,443,519 A * | 8/1995 | Averill et al. .............. 623/22.22 |
| 5,462,563 A | 10/1995 | Shearer et al. |
| 5,507,817 A | 4/1996 | Craig et al. |
| 5,507,818 A | 4/1996 | McLaughlin |
| 5,507,824 A | 4/1996 | Lennox |
| 5,549,682 A | 8/1996 | Roy |
| 5,580,352 A | 12/1996 | Sekel |
| 5,702,447 A | 12/1997 | Walch et al. |
| 5,702,457 A | 12/1997 | Walch et al. |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,807 A | 5/1998 | Anstaett et al. |
| 5,800,551 A | 9/1998 | Williamson et al. |
| 5,879,405 A | 3/1999 | Ries et al. |
| 5,902,340 A | 5/1999 | White et al. |
| 5,910,171 A | 6/1999 | Kummer et al. |
| 5,928,285 A | 7/1999 | Bigliani et al. |
| 5,944,758 A | 8/1999 | Mansat et al. |
| 5,961,555 A | 10/1999 | Huebner |
| 5,984,927 A | 11/1999 | Wenstrom, Jr. et al. |
| 6,015,437 A | 1/2000 | Stossel |
| 6,033,439 A | 3/2000 | Camino et al. |
| 6,045,582 A | 4/2000 | Prybyla |
| 6,045,583 A | 4/2000 | Gross et al. |
| 6,102,953 A | 8/2000 | Huebner |
| 6,129,764 A | 10/2000 | Servidio |
| 6,165,224 A | 12/2000 | Tornier |
| 6,171,341 B1 | 1/2001 | Boileau et al. |
| 6,197,062 B1 | 3/2001 | Fenlin |
| 6,197,063 B1 | 3/2001 | Dews |
| 6,203,575 B1 | 3/2001 | Farey |
| 6,206,925 B1 | 3/2001 | Tornier |
| 6,228,120 B1 | 5/2001 | Leonard et al. |
| 6,267,767 B1 | 7/2001 | Strobel et al. |
| 6,283,999 B1 | 9/2001 | Rockwood, Jr. |
| 6,312,467 B1 | 11/2001 | McGee |
| 6,334,874 B1 | 1/2002 | Tornier et al. |
| 6,364,910 B1 | 4/2002 | Shultz et al. |
| 6,368,352 B1 | 4/2002 | Camino et al. |
| 6,368,353 B1 | 4/2002 | Arcand |
| 6,398,812 B1 | 6/2002 | Masini |
| 6,406,495 B1 | 6/2002 | Schoch |
| 6,406,496 B1 | 6/2002 | Rüter |
| 6,436,144 B1 | 8/2002 | Ahrens |
| 6,436,147 B1 | 8/2002 | Zweymuller |
| 6,458,136 B1 | 10/2002 | Allard et al. |
| 6,475,243 B1 | 11/2002 | Sheldon et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,514,287 B2 | 2/2003 | Ondrla et al. |
| 6,520,994 B2 | 2/2003 | Nogarin |
| 6,530,957 B1 | 3/2003 | Jack |
| 6,558,425 B2 | 5/2003 | Rockwood |
| 6,569,202 B2 | 5/2003 | Whiteside |
| 6,589,281 B2 | 7/2003 | Hyde, Jr. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,736,851 B2 | 5/2004 | Maroney et al. |
| 6,746,487 B2 | 6/2004 | Scifert et al. |
| 6,749,637 B1 | 6/2004 | Bahler |
| 6,755,866 B2 | 6/2004 | Southworth |
| 6,761,740 B2 | 7/2004 | Tornier |
| 6,780,190 B2 | 8/2004 | Maroney |
| 6,783,549 B1 | 8/2004 | Stone et al. |
| 6,790,234 B1 | 9/2004 | Frankle |
| 6,875,234 B2 | 4/2005 | Lipman et al. |
| 6,887,277 B2 | 5/2005 | Rauscher et al. |
| 6,890,358 B2 | 5/2005 | Ball et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,033,396 B2 | 4/2006 | Tornier |
| 7,066,959 B2 | 6/2006 | Errico |
| 7,108,719 B2 | 9/2006 | Horber |
| 7,169,184 B2 | 1/2007 | Dalla Pria |
| 7,175,663 B1 | 2/2007 | Stone |
| 7,238,208 B2 | 7/2007 | Camino et al. |
| 7,297,163 B2 | 11/2007 | Huebner |
| 7,329,284 B2 | 2/2008 | Maroney et al. |
| 7,338,528 B2 | 3/2008 | Stone et al. |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0099381 A1 | 7/2002 | Maroney |
| 2002/0138148 A1 | 9/2002 | Hyde, Jr. |
| 2002/0143402 A1 | 10/2002 | Steinberg |
| 2002/0151982 A1 | 10/2002 | Masini |
| 2003/0009171 A1 | 1/2003 | Tornier |
| 2004/0006392 A1 | 1/2004 | Grusin et al. |
| 2004/0034431 A1 | 2/2004 | Maroney et al. |
| 2004/0064187 A1 | 4/2004 | Ball et al. |
| 2004/0064190 A1 | 4/2004 | Ball et al. |
| 2004/0122520 A1 | 6/2004 | Lipman et al. |

(56) References Cited

U.S. PATENT DOCUMENTS

| | | |
|---|---|---|
| 2004/0133276 A1 | 7/2004 | Lang et al. |
| 2004/0138754 A1 | 7/2004 | Lang et al. |
| 2004/0148033 A1 | 7/2004 | Schroeder |
| 2004/0186579 A1 | 9/2004 | Callaway et al. |
| 2004/0193275 A1 | 9/2004 | Long et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210317 A1 | 10/2004 | Maroney et al. |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0267370 A1 | 12/2004 | Ondrla |
| 2005/0008672 A1 | 1/2005 | Winterbottom et al. |
| 2005/0010301 A1 | 1/2005 | Disilvestro et al. |
| 2005/0015154 A1 | 1/2005 | Lindsey et al. |
| 2005/0033443 A1 | 2/2005 | Blatter et al. |
| 2005/0043805 A1 | 2/2005 | Chudik |
| 2005/0049709 A1 | 3/2005 | Tornier |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondrla et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0209700 A1 | 9/2005 | Rockwood et al. |
| 2005/0216092 A1 | 9/2005 | Marik et al. |
| 2005/0251263 A1 | 11/2005 | Forrer et al. |
| 2005/0256584 A1* | 11/2005 | Farrar ................. 623/22.15 |
| 2005/0267590 A1 | 12/2005 | Lee |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0020344 A1* | 1/2006 | Shultz et al. ............ 623/19.12 |
| 2006/0030946 A1 | 2/2006 | Ball et al. |
| 2006/0241775 A1 | 10/2006 | Buss |
| 2007/0225817 A1 | 9/2007 | Reubelt et al. |
| 2007/0225821 A1 | 9/2007 | Reubelt et al. |
| 2007/0244564 A1 | 10/2007 | Ferrand et al. |
| 2007/0250174 A1 | 10/2007 | Tornier et al. |

FOREIGN PATENT DOCUMENTS

| | | |
|---|---|---|
| DE | 19509037 | 9/1996 |
| DE | 19630298 | 1/1998 |
| EP | 0257359 | 3/1988 |
| EP | 0299889 | 1/1989 |
| EP | 0524857 | 1/1993 |
| EP | 0549480 | 6/1993 |
| EP | 0599429 | 6/1994 |
| EP | 0617934 | 10/1994 |
| EP | 0664108 | 7/1995 |
| EP | 0679375 | 11/1995 |
| EP | 0712617 | 5/1996 |
| EP | 0715836 | 6/1996 |
| EP | 0797694 | 10/1997 |
| EP | 0807426 | 11/1997 |
| EP | 0809986 | 12/1997 |
| EP | 0864306 | 9/1998 |
| EP | 0903127 | 3/1999 |
| EP | 0903128 | 3/1999 |
| EP | 0927548 | 7/1999 |
| EP | 1062923 | 12/2000 |
| EP | 1064890 B1 | 1/2001 |
| EP | 1195149 | 4/2002 |
| EP | 1380274 | 1/2004 |
| EP | 1402854 | 3/2004 |
| FR | 2248820 | 5/1975 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2721200 | 12/1995 |
| FR | 2726994 | 5/1996 |
| FR | 2737107 | 1/1997 |
| FR | 2832922 A | 6/2003 |
| FR | 2835425 | 8/2003 |
| FR | 2836039 | 8/2003 |
| GB | 2325626 A | 12/1998 |
| SU | 749392 | 7/1980 |
| WO | WO 91/07932 | 6/1991 |
| WO | WO 93/09733 | 5/1993 |
| WO | WO 96/17553 | 6/1996 |
| WO | WO 98/46172 | 10/1998 |
| WO | WO 99/49792 | 10/1999 |
| WO | WO 99/65413 | 12/1999 |
| WO | WO 00/15154 | 3/2000 |
| WO | WO 00/41653 | 7/2000 |
| WO | WO 01/47442 | 7/2001 |
| WO | WO 02/39931 | 5/2002 |
| WO | WO 02/39933 | 5/2002 |
| WO | WO 02/067821 | 9/2002 |
| WO | WO 03/005933 | 1/2003 |
| WO | WO03/094806 | 11/2003 |
| WO | WO 2007/109319 | 2/2007 |
| WO | WO 2007/109291 | 9/2007 |
| WO | WO 2007/109340 | 9/2007 |

OTHER PUBLICATIONS

"Anatomical Shoulder™—Cemented Shoulder Prosthesis Product Information and Surgical Technique," Sulzer Medica, 2000.

"Anatomical Shoulder™ System—the new removable head option," Zimmer, Inc., 2004.

"Anatomical Shoulder™ System Surgical Technique—Removeable head option for improved surgical results," Zimmer, Inc., 2004.

Apoil, André. "A Condyle for the Rotator Cuff Muscles, the total shoulder prosthesis," Aesculap®, 1994.

"Bigliani/Flatow®—The complete shoulder solution—designed by shoulder surgeons for shoulder surgery," Zimmer, Inc., 2001.

Boileau, et al. "Adaptability and modularity of shoulder prosthese," *Maitrise Orthopédique*, http://www.maitrise-orthop.com/corpusmaitri/orthopaedic/prothese_epaule_orthop/boileau_us.shtml, Jan. 3, 2006.

"Bio-Modulare®/ Bi-Polar Shoulder Arthroplasty," Biomet, Inc., 1997.

Beuchel M.D., Frederick F. "Beuchel-Pappas™ Modular Salvage Shoulder System," Endotec, Inc., 2000.

Beuchel M.D., Frederick F. "Beuchel-Pappas™ Resurfacing Shoulder System," Endotec, Inc., 2000.

Beuchel M.D., Frederick F. "Beuchel-Pappas™ Total Shoulder System," Endotec, Inc., 2000.

"Copeland™ Humeral Resurfacing Head," Biomet Orthopedics, Inc., 2001.

"Delta CTA™ Reverse Shoulder Prosthesis," DePuy International, Ltd., 2004.

"Global C.A.P.™ Surgical technique, resurfacing humeral head implant," DePuy International, Ltd., 2004.

Hertel M.D., PD, Ralph. "Technical considerations for implantation of EPOCA glenoid components (Leseprobe)," *Epoca Newsletter*, May 14, 2001.

Klein, Travis J., et al. "Mechanically favorable bone remodeling in rotator cuff arthropathy patients with good funtion," *Minneapolis Sports Medicine Center and University of Minnesota*.

Mansat, Michel. "Neer 3™, Surgical Technique for Fractures," Smith & Nephew, 2000.

Molé, M.D., et al. "Aequalis-Reversed™ Shoulder Prosthesis, Surgical Technique," Tornier, Inc.

Nicholson, Gregory P., "Arthroplasty and Rotator Cuff Deficiency," Chapter 7, pp. 149-166.

(56) References Cited

OTHER PUBLICATIONS

"Offset Head, Bio-Modular® Total Shoulder," Biomet, Inc., 2000.
"The Foundation® Total Shoulder System," Encore Surgical.
"Tornier Surgical Technique Addendum, Tornier Aequalis® Reversed Hemi-Adaptor Technique," Tornier, Inc., Aug. 8, 2005.
"Tornier Surgical Technique Addendum, Aequalis® Reversed Shoulder Polyethylene Insert," Tornier, Inc., Aug. 8, 2005.
Boileau et al., U.S. Appl. No. 12/020,913, entitled "Method and Apparatus for Fitting a Shoulder Prosthesis" filed Jan. 28, 2008.
John M. Fenlin Jr., M.D., Symposium on Surgery of the Shoulder, "Total Glenohumeral Joint Replacement," *Orthopedic Clinics of North America*, vol. 6, No. 2, Apr. 1975, pp. 565-583.
"Aequalis-Fracture Suture Technique in 5 Steps," Tornier, Inc.
"Aequalis-Fracture Shoulder Prosthesis—Surgical Technique," Tornier, Inc.
"Aequalis® Press-Fit Shoulder Prosthesis—Surgical Technique," Tornier, Inc.
Bigliani/Flatow®—The Complete Shoulder Solution, 4-Part Fracture of the Humerus Surgical Technique, Zimmer, Inc., 2000.
"Bio-Modular® Choice, Shoulder System," Biomet Orthopedics, Inc., 2004.
"Bio-Modular Total Shoulder Surgical Technique," Biomet Orthopedics, Inc., 2001.
Boileau, et al. "Arthroscopic Repair of Full-Thickness Tears of the Supraspinatus: Does the tendon really heal?," *The Journal of Bone and Joint Surgery, Inc.*, pp. 1229-1240, 2005.
"Design Rationale," Latitude®.
"The Townley Modular Shoulder, Design by Reason," Biopro, Inc.
Zimmer® Bigliani/Flatow®—The Complete Shoulder Solution, Total Shoulder Arthroplasty Surgical Technique, Zimmer, Inc., 2003.
"Zimmer® Shoulder Retractors, "Zimmer, Inc., 2000.
Cofield, M.D., Robert H. "Cofield[2] Total Shoulder System, Surgical Technique," Smith & Nephew, 1997.
"Aequalis®-Glenoid Keeled and Pegged—Surgical Technique," Tornier, Inc.
International Search Report and Written Opinion from related International Patent Application No. PCT/US07/06961 dated Dec. 13, 2007.
"Tornier Aequalis® Reversed 2 Prong Capsular Retractor," Tornier, Inc., Oct. 8, 2005.
"Tornier Aequalis® Reversed Shoulder G2 Baseplate," Tornier, Inc., Oct. 8, 2005.
International Search Report and Written Opinion issued in PCT/US2007/06961, mailed Dec. 13, 2007, 12 pages.
Supplementary European Search Report issued in EP 07753578, mailed Nov. 30, 2009, 6 pages.

\* cited by examiner

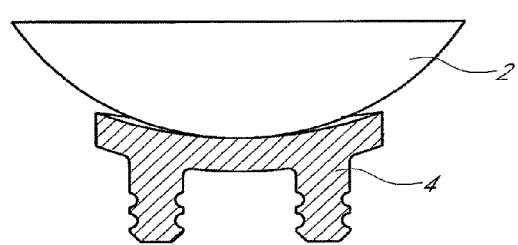
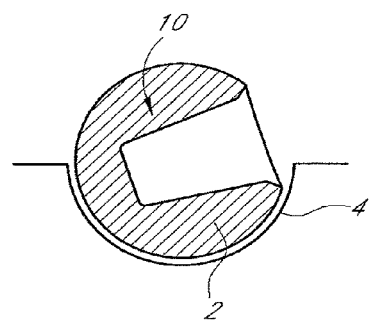
*FIG. 1A*
(PRIOR ART)
*FIG. 1B*
(PRIOR ART)
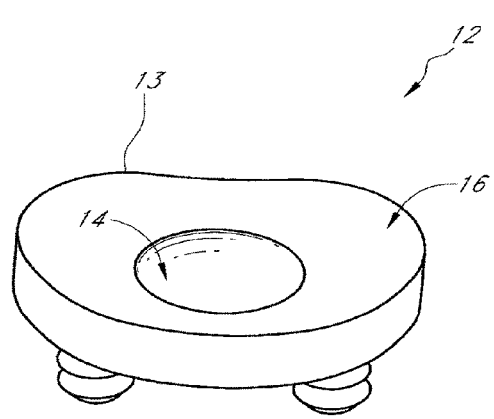
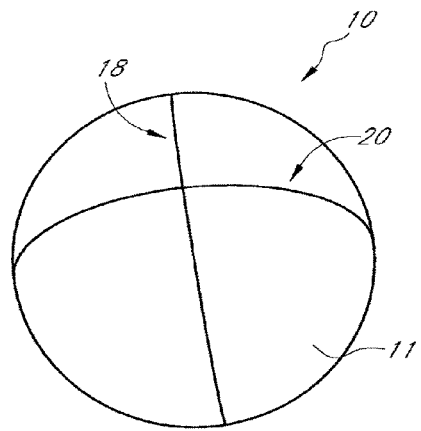
*FIG. 1C*
*FIG. 1D*

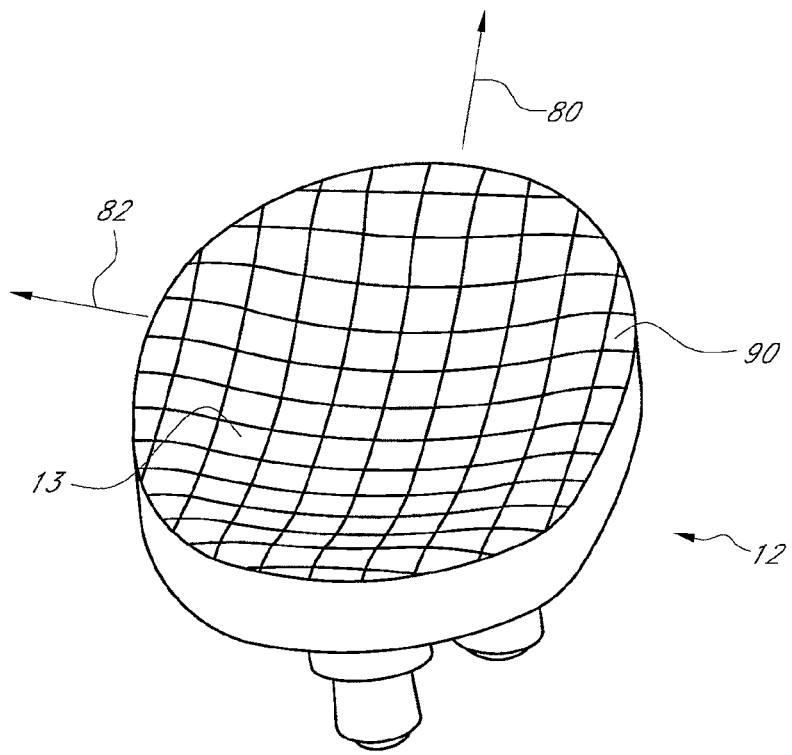
FIG. 13
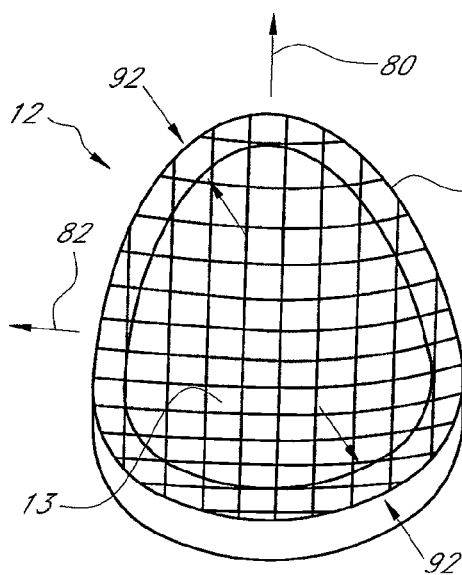 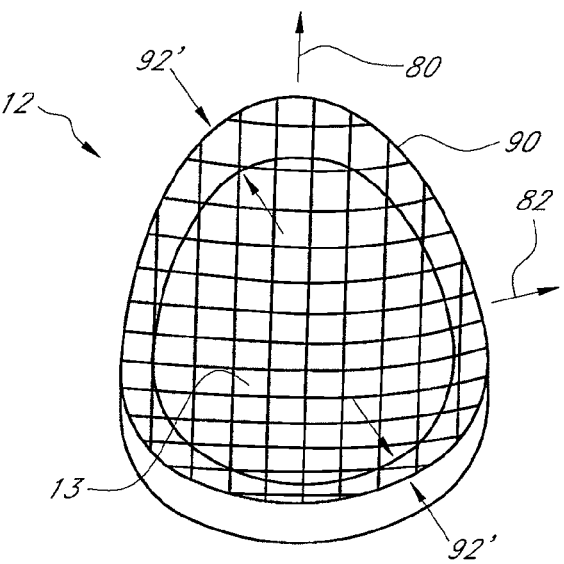
FIG. 14A  FIG. 14B

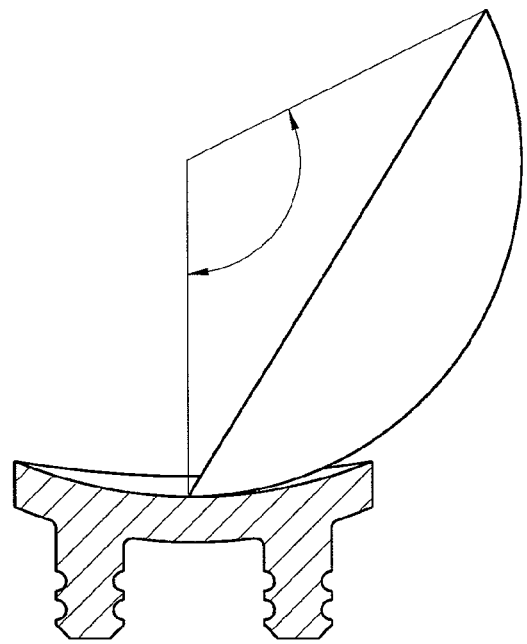
FIG. 17
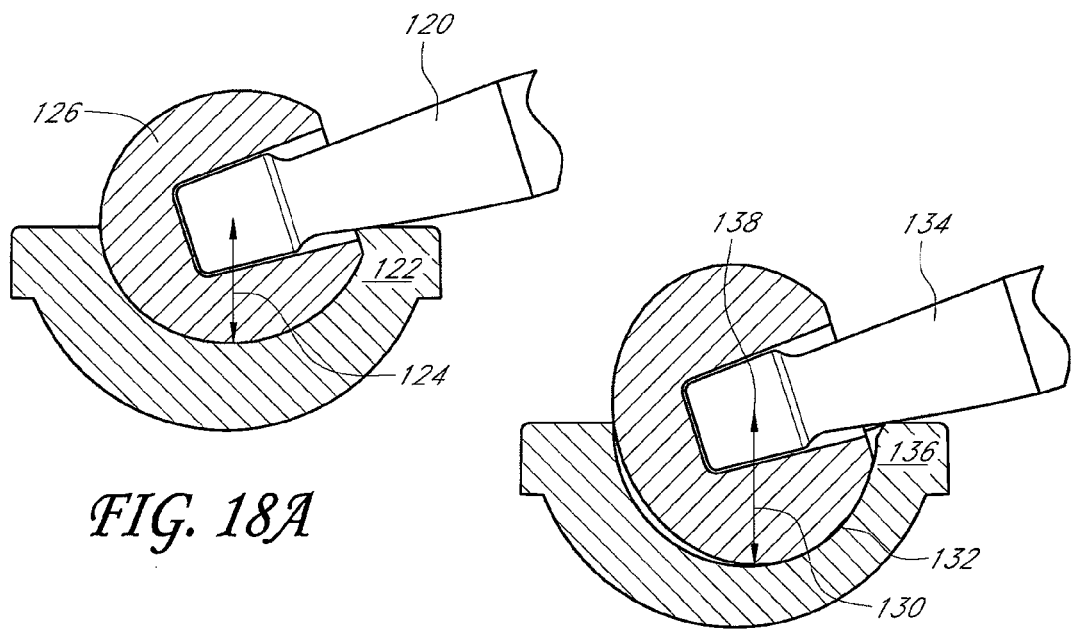
FIG. 18A
FIG. 18B

NON-SPHERICAL ARTICULATING SURFACES IN SHOULDER AND HIP REPLACEMENT

CROSS-REFERENCE TO RELATED APPLICATIONS

The present application is based on and claims priority under 35 U.S.C. §119(e) to U.S. Provisional Application No. 60/784,238, filed on Mar. 21, 2006, the entire contents of which are expressly incorporated by reference herein.

BACKGROUND

1. Field of the Inventions

The present inventions relate to orthopedic joint replacements, and more specifically, to orthopedic devices that incorporate non-spherical articulating surfaces and a method of making and fitting such devices.

2. Description of the Related Art

Anatomically, a joint typically refers to a movable junction in the body of a subject between two or more bones. As used herein, the term is meant to include the different kinds of ligaments, tendons, cartilages, bursae, synovial membranes and bones comprising the mobile skeletal system of a subject in various quantities and configurations.

For example, the hip joint essentially is a ball and socket joint, linking the "ball" at the head of the thigh bone (femur) with the cup-shaped "socket" (acetabulum) in the pelvic bone. The ball normally is held in the socket by powerful ligaments that form a complete sleeve around the joint (the joint capsule). The joint capsule has a delicate lining (the synovium). Cartilage, which covers the head of the femur and lines the socket, cushions the joint, and allows the bones to move on each other with very little friction.

In a normal hip joint, the substantially spherical head of the thighbone (femur) moves inside the acetabulum of the pelvis. Normally, these components work in harmony. But disease or injury can disrupt this harmony, resulting in pain, muscle weakness and less function, necessitating a total hip replacement. Several manufacturers make total hip replacement implants, which typically have three parts: the stem, which fits into the femur and provides stability; the ball, which replaces the spherical head of the femur; and the cup, which replaces the worn-out hip socket. Each part comes in various sizes in order to accommodate various body sizes and types. In some designs, the stem and ball are one piece; other designs are modular, allowing for additional customization in fit.

The shoulder joint is the body's most mobile joint, in that it can turn in many directions. The shoulder is a ball-and-socket joint made up of three bones: the upper arm bone (humerus), shoulder blade (scapula) and collarbone (clavicle). Two joints facilitate shoulder movement. The acromioclavicular (AC) joint joins one end of the collarbone with the shoulder blade; it is located between the acromion (the part of the scapula that forms the highest point of the shoulder) and the clavicle. The other end of the collarbone is joined with the breastbone (sternum) by the sternoclavicular joint. The glenohumeral joint, commonly called the shoulder joint, is a ball-and-socket type joint that helps move the shoulder forward and backward and allows the arm to rotate in a circular fashion or hinge out and up away from the body. The ball, or head, of the glenohumeral joint is the top, rounded portion of the humerus; the socket, or glenoid, is a dish-shaped part of the outer edge of the scapula into which the ball fits. The socket of the glenoid is surrounded by a soft-tissue ring of fibrocartilage (the glenoid labrum) that runs around the cavity of the scapula (glenoid cavity) in which the head of the humerus fits. The labrum deepens the glenoid cavity and effectively increases the surface of the shoulder joint, which helps stabilize the joint.

The bones of the shoulder are held in place by muscles, tendons (tough cords of tissue that attach the shoulder muscles to bone and assist the muscles in moving the shoulder) and ligaments (bands of fibrous tissue that connects bone to bone or cartilage to bone, supporting or strengthening a joint). A smooth, durable surface (the articular cartilage) on the head of the arm bone, and a thin lining (synovium) allows smooth motion of the shoulder joint. The joint capsule, a thin sheet of fibers that encircles the shoulder joint, allows a wide range of motion yet provides stability of the joint. The capsule is lined by a thin, smooth synovial membrane. The front of the joint capsule is anchored by three glenohumeral ligaments.

The rotator cuff, a structure composed of tendons and associated muscles that holds the ball at the top of the humerus in the glenoid socket, covers the shoulder joint and joint capsule. The rotator cuff provides mobility and strength to the shoulder joint. A sac-like membrane (bursa) between the rotator cuff and the shoulder blade cushions and helps lubricate the motion between these two structures.

The shoulder is an unstable joint easily subject to injury because of its range of motion, and because the ball of the humerus is larger than the glenoid that holds it. To remain stable, the shoulder must be anchored by its muscles, tendons and ligaments. Some shoulder problems arise from the disruption of these soft tissues due to injury or overuse, or underuse of the shoulder. Other problems can arise from degenerative processes.

For example, instability of the shoulder joint refers to situations that occur when one of the shoulder joints moves or is forced out of its normal position. The two basic forms of shoulder instability are subluxations and dislocations. A partial or incomplete dislocation of the shoulder joint (subluxation) means the head of the humerus is partially out of the socket (glenoid). A complete dislocation of the shoulder joint means that the head of the humerus is completely out of the socket. Anterior instability, for example, refers to a type of shoulder dislocation where the shoulder slips forward, meaning that the humerus moved forward and down out of its joint. Anterior instability may occur when the arm is placed in a throwing position. Both partial and complete dislocation cause pain and unsteadiness in the shoulder joint. Patients with repeat dislocation usually require surgery.

Bursitis or tendonitis can occur with overuse from repetitive activities, which cause rubbing or squeezing (impingement) of the rotator cuff under the acromion and in the acromioclavicular joint. Partial thickness rotator cuff tears, most often the result of heavy lifting or falls, can be associated with chronic inflammation and the development of spurs on the underside of the acromion or the AC joint. Full thickness rotator cuff tears most often are the result of impingement.

Osteoarthritis and rheumatoid arthritis can cause destruction of the shoulder joint and surrounding tissue and degeneration and tearing of the capsule or rotator cuff. In osteoarthritis, the articular surface of the joint wears thin. Rheumatoid arthritis is associated with chronic inflammation of the synovium lining, which can produce substances that eventually destroy the inner lining of the joint, including the articular surface.

Shoulder replacement is recommended for subjects with painful shoulders and limited motion. The treatment options are either replacement of the head of the humerus or replacement of the entire socket. However, available treatment options are less than adequate in restoring shoulder joint function. If the humeral or femoral head is to be replaced it is typically replaced by a resurfacing component, which replaces just the surface of the head or by a full head, which is typically fixed to a stem which is, in turn implanted into the humerus or femur for stability. When a reverse humerus is used, it is typically fixed to a humeral stem. For glenoid replacement a bearing surface is typically implanted directly into the scapula or fixed to a metal back, which is implanted into the scapula. A reverse glenoid replacement is typically fixed onto a metal back which is implanted into the scapula.

Most current shoulder and hip replacement components on the market consist of essentially spherical on spherical articulation. However, to achieve optimal results, different activities require different levels of constraint, joint thickness, soft tissue tension, moment, and arc of motion. Spherical articulation does not take this into account and therefore can not provide optimal results.

Exceptions to the typical spherical configurations that do exist have been limited to certain shoulder dual radius designs that incorporate either different inferior/superior and anterior/posterior radii, or different central and peripheral radii, both of which have been applied to both the glenoid and humeral head. While these dual radius designs may offer marginal improvements, they are still generalizations and do not account for the kinematic requirements of specific activities.

SUMMARY OF THE INVENTIONS

According to an embodiment of the present inventions, an orthopedic device is provided for joint reconstruction. The device comprises a head component comprising a generally convex head surface and/or a bearing component comprising a generally concave bearing surface. At least one of the generally convex head surface or the generally concave bearing surface comprises a continuously varying curvature.

Another embodiment of the present inventions relate to an orthopedic device for joint reconstruction. The device comprises a head component comprising a generally convex head surface and/or a bearing component comprising a generally concave bearing surface. At least one of the generally convex head surface or the generally concave bearing surface comprises a non-spherical surface configured to improve with respect to a spherical surface at least one of a constraint level, soft tissue tension, moment or arc of motion of a subject's joint.

In accordance with another embodiment, the non-spherical articulating surface of the bearing component can be substantially concave. Further, the non-spherical articulating surface of the head component can be substantially convex. The non-spherical articulating surface of the head component can articulate with a coupling mechanism that can mate with the supportive substrate. In this regard, the coupling mechanism can be selected from the group consisting of a taper, a screw, a locking mechanism, a peg, a keel, and a screw.

The bearing component can be one of a glenoid resurfacing component, a reverse humeral bearing, and an acetabular bearing. The head component can be one of a humeral head, a femoral head, a reverse glenosphere, a humeral resurfacing component, and a femoral resurfacing component. The supportive substrate can be one of a humeral stem, a femoral stem, a glenosphere base plate, a glenoid bone, a reverse humeral stem, a humeral bone, a femoral bone, and an acetabular cup. The fixation mechanism can be one of a cemented glenoid peg, a locking mechanism for a reverse humeral stem, and a locking mechanism for an acetabular cup.

Another embodiment of the present inventions relate to a method of forming an orthopedic reconstructive joint replacement for a joint utilizing an orthopedic device. The method includes providing a non-spherical articulating surface on a head component, providing an optional bearing component, and configuring the non-spherical surface on the head component to adjust at least one variable selected from the group consisting of constraint, joint thickness, soft tissue tension, moment, and arc of motion as compared to a spherical surface.

BRIEF DESCRIPTION OF THE DRAWINGS

FIG. 1A shows an example of a prior art spherical radius head component used for a shoulder joint.

FIG. 1B shows an example of a prior art spherical radius head component used for a hip joint.

FIG. 1C shows an example of a prior art bearing component having a central radius that is different from its peripheral radius, according to an embodiment of the present inventions.

FIG. 1D shows an example of a prior art head component having an inferior/superior radius that is different from its anterior/posterior radius, according to an embodiment.

FIG. 13 is a perspective view of another embodiment of the bearing component illustrating a local convex curvature applied around a periphery thereof.

FIG. 14A is a top view of yet another embodiment of the bearing component illustrating a local convex curvature whose size and shape is consistent around the periphery thereof.

FIG. 14B is a top view of yet another embodiment of the bearing component illustrating a local convex curvature whose size and shape is varied around the periphery thereof.

FIG. 17 shows a humeral head flexed to the edge of its arc of motion, according to an embodiment.

FIG. 18A is an illustration of how a spherical femoral head causes impingement of a femoral neck against an acetabular bearing.

FIG. 18B is an illustration of how a non-spherical femoral head can prevent and/or eliminate impingement of a femoral neck against an acetabular bearing, according to an embodiment.

DETAILED DESCRIPTION OF THE PREFERRED EMBODIMENTS

Figure 2:
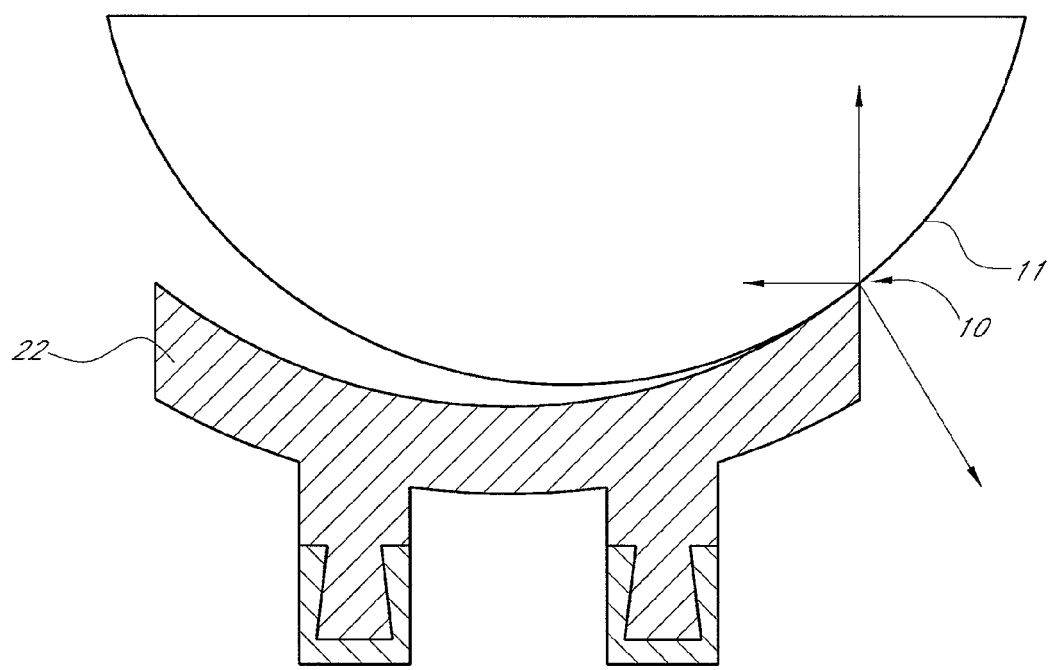
FIG. 2 is a side view of a prior art glenoid joint illustrating an unsupported load.

The embodiments described herein relate generally to orthopedic joint replacements, and more specifically, to orthopedic devices that incorporate complex, non-spherical articulating surfaces and a method of making and fitting such devices. By incorporating such surfaces, the embodiments disclosed herein can provide a greater available range of motion and other benefits for a joint when compared with existing artificial shoulder joint and artificial hip joints.

According to some embodiments, a complex, non-spherical articulating surface can be incorporated on a humeral head and/or glenoid of a shoulder prosthesis or reverse glenosphere and/or reverse humeral cup. In other embodiments, a complex, nonspherical articulating surface can be incorporated on the acetabulum and/or femoral head of a hip prosthesis. As disclosed herein, such embodiments of the non-spherical surface can be used to adjust constraint, joint thickness, soft tissue tension, moment and arc of motion, and in doing so, influence motion of the joint.

As used herein, the following anatomical terms shall be defined as follows. The term "subject" as used herein includes animals of mammalian origin, including humans. When referring to animals that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is a Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, and lateral structures are farther from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

A symmetric subject is assumed when the terms "medial," "lateral," "inferior," "superior," "anterior," and "posterior," are used to refer to an implant.

As used herein, the term "articulate" means to associate, join, link, or otherwise connect by a joint, at least two components together such that there is relative motion between the two components. An "articulating surface" is a superficial aspect of a first bone at the joint formed by a first bone and a second bone. At the joint, the articulating surface of the first bone associates with the articulating surface of the second bone.

As will be described below, the articulating components of both shoulder and hip replacement systems can comprise a substantially convex ("head") surface that articulates with respect a substantially concave ("bearing") surface. The term "convex," as used herein, refers to a surface that is curving or bulging outward. The term "concave," as used herein, refers to a surface that is curving inward. Because embodiments disclosed herein can be used for any shoulder or hip articulating component (e.g., traditional or reverse configurations), the term "bearing" can be used herein to refer to any substantially concave surface, and the term "head" can be used herein to refer to any substantially convex surface unless further differentiation is required.

Reference will now be made to the drawings, which are used for illustrating embodiments of the present inventions and not for purposes of limiting the same. FIGS. 1A-B are side view of prior art shoulder (FIG. 1A) and hip joints (FIG. 1B), respectively, wherein a spherical head 2 mates with a spherical bearing 4, as described above. FIGS. 1C-D illustrate existing marginal improvements on spherical articulation. Specifically, FIG. 1C illustrates a glenoid whose central radius 14 is different from its peripheral radius 16 while FIG. 1D shows a head 10 with a longitudinal radius 18 that is different from its transverse radius 20. In contrast, as will be described herein, the illustrated embodiments of a head component 10 and a bearing component 12 can be configured to include non-spherical, complex articulating surfaces 11, 13, respectively, for providing varying constraint, soft tissue tension, moment, and/or arc of motion, as required by various activities. See e.g., FIG. 5C and FIG. 13.

The concepts illustrated in the head component 10 and bearing component 12 can be utilized in a prosthesis for a shoulder or hip joint. In use, a particular activity of the shoulder prosthesis may be otherwise limited if the (humeral) head component 10 is not allowed to translate as much as required. As such, the curvature of the articulating surface 13 of the bearing component 12 or glenoid articulating surface can be made locally less constraining to allow the desired motion in the desired direction while maintaining constraint levels in other areas of the glenoid. See e.g., FIG. 27. Similarly, the local radius of curvature of the head component 10 can be reduced to provide less conformity with the bearing and allow more motion. See e.g., FIG. 31.

As mentioned above, the head component 10 and/or the bearing component 12 can include non-spherical, complex articulating surfaces. As used herein, a "non-spherical, complex" surface can be characterized by a continuously varying curvature and/or a curvature created using curves that are defined by 3 or preferably 4 or more connecting radii. As will be described, embodiments of the non-spherical complex surfaces disclosed herein can be used to advantageously locally vary constraint level, soft tissue tension, moment, or arc of motion.

To understand the advantages of the embodiments described herein "constraint level," "soft tissue tension," "moment," and "arc of motion" will now be described in more detail. As shown in FIG. 2, head translation in glenoid joint movement is typically opposed or "constrained" by a reaction force caused by a bearing component 22. As used herein, the term "constraint" refers to the resistance (meaning any mechanical force that tends to retard or oppose motion) to translation (meaning a uniform movement without rotation) of one body with respect to another. "Soft tissue tension" refers to a measure of the strain in the soft tissue that imparts a force to a body. Additionally, if the moment arm $M_a$ is measured from the point of force application to the point of contact with the bearing, it can refer to rolling moment, which is a measure of what would be required to roll the head instead of pivot the head.

"Moment" will be described with reference to FIG. 3, which illustrates one embodiment of a joint 28 wherein a head component 10 articulates with a bearing component 12. In the illustrated embodiment, a "moment" of force is a quantity that represents a magnitude of force 30 applied to a rotational system at a distance 32 from an axis of rotation 34. This characteristic distance 32 generally is termed the "moment arm." As used herein, the term "moment arm" refers to the normal distance from an instantaneous center of curvature 36 of the head 10 to the application vector of the force 30. Generally, the moment M of a force vector D is represented as $M=M_a \times D$, where $M_a$ is the moment arm and D is the magnitude of the force applied. As will be appreciated by one of skill in the art, increasing the distance 32 reduces the force 30 required to flex the joint.

Figure 4:
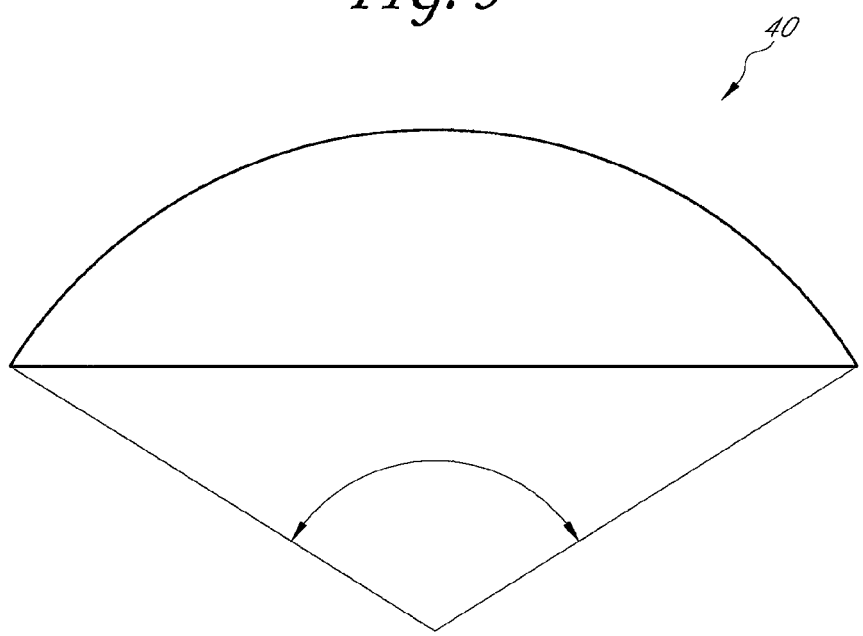
FIG. 4 shows an illustration of an arc of motion, according to an embodiment.

With reference to FIGS. 4 and 17, the term "arc of motion" refers to the angle to which the surface can articulate until physically limited by an edge of the surface of a bearing or head component.

Figure 3:
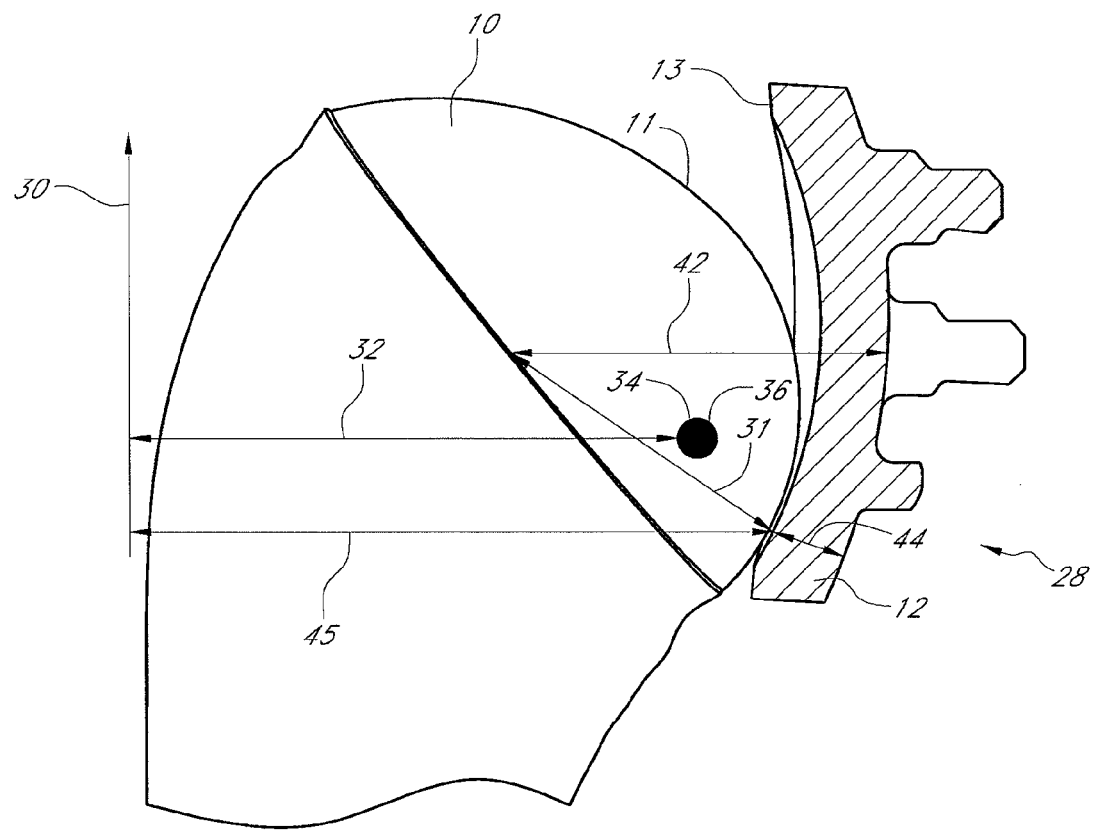
FIG. 3 is a moment diagram illustrating a moment created about a center of curvature in a joint, according to an embodiment.

A joint 28 is also shown in FIG. 3 to illustrate joint thickness 42. As used herein, the term "joint thickness" refers to the distance between centrally fixed points on each component of a joint 28 at a particular articulation position. Component thickness refers to the local thickness of a joint component, such as the glenoid 12 or head component 10. Local thickness 44 of the bearing/glenoid component 12 refers to the distance from the articulating surface to the supportive substrate in a given area. Local thickness 31 of a head component 10 refers to the distance from a defined center point to a given point on the articulating surface. Increasing component thickness 44, 31 can tend to increase joint thickness 42. Increasing or decreasing joint thickness 42 would increase or decrease soft tissue tension accordingly. This change in soft tissue tension would change the kinematic characteristics of the joint. If this joint thickness were changed only when the joint was in a certain position, the kinematics could be customized for different activities. Joint thickness 42 could be locally changed by locally changing the component thickness using complex non-spherical surfaces.

Additionally, FIGS. 18A and 18B illustrate that the local head thickness may be increased to avoid impingement. Increasing the local head thickness would tend to increase the joint thickness (move the neck farther away from the cup), thus allowing further articulation before the neck impinges on the cup. With reference back to FIG. 3, increasing the joint thickness 42 may increase the rolling moment arm 45 of the device by increasing the distance from the force application to the joint articulation point.

Figure 6:
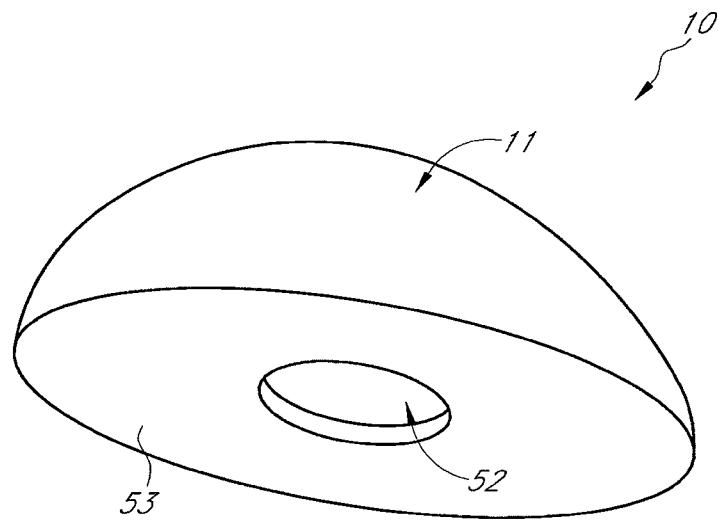
FIG. 6 is a perspective bottom view of an exemplary embodiment of the head component.
Figure 7:
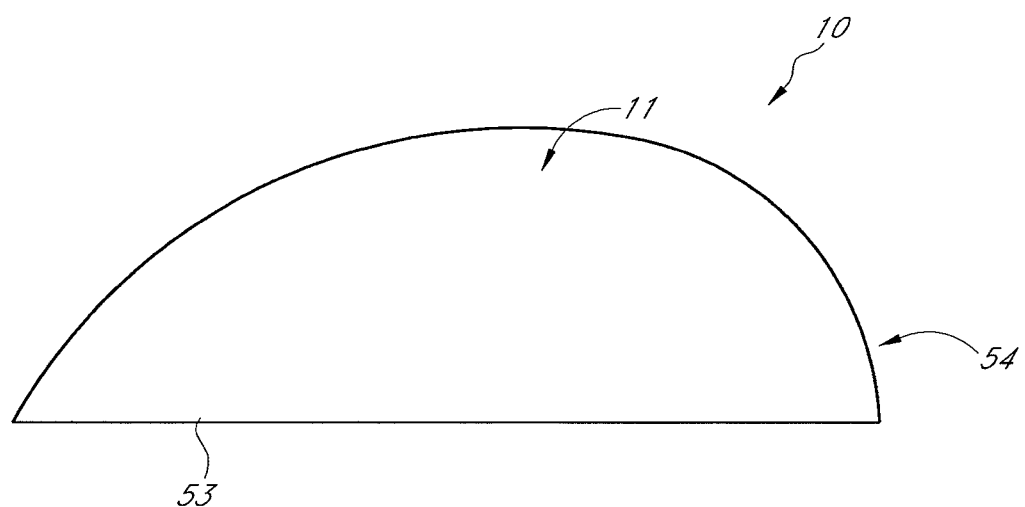
FIG. 7 is a side view of the head component of FIG. 6 illustrating locally varied curvature.
Figure 8:
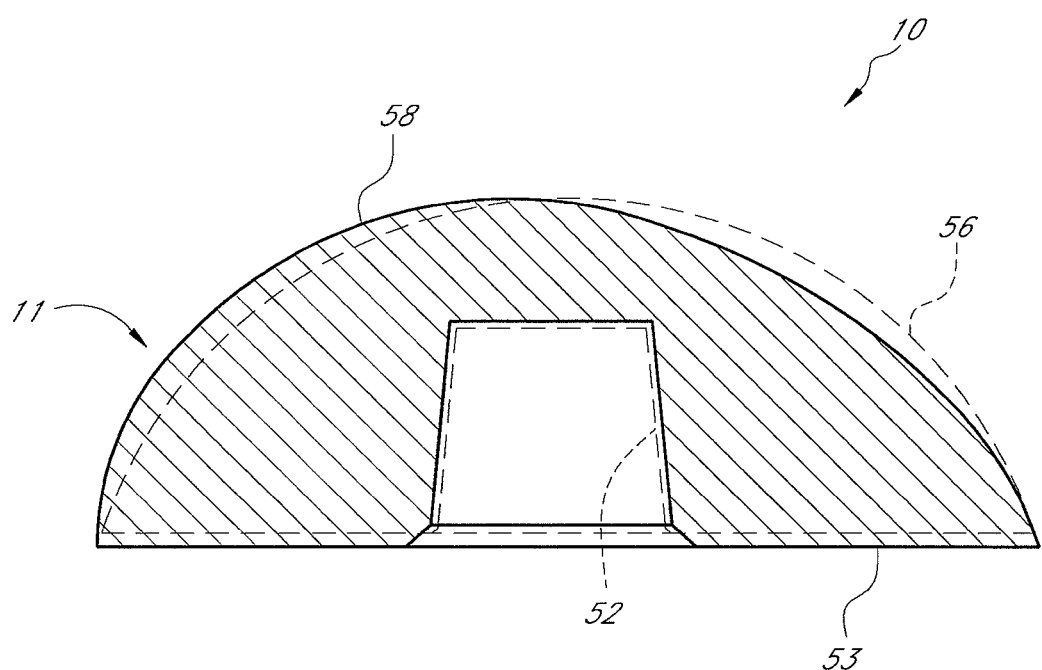
FIG. 8 is a side cross-sectional view of an exemplary embodiment of the head component compared to a spherical humeral head (shown in dashed lines).
Figures 9A, 9B:
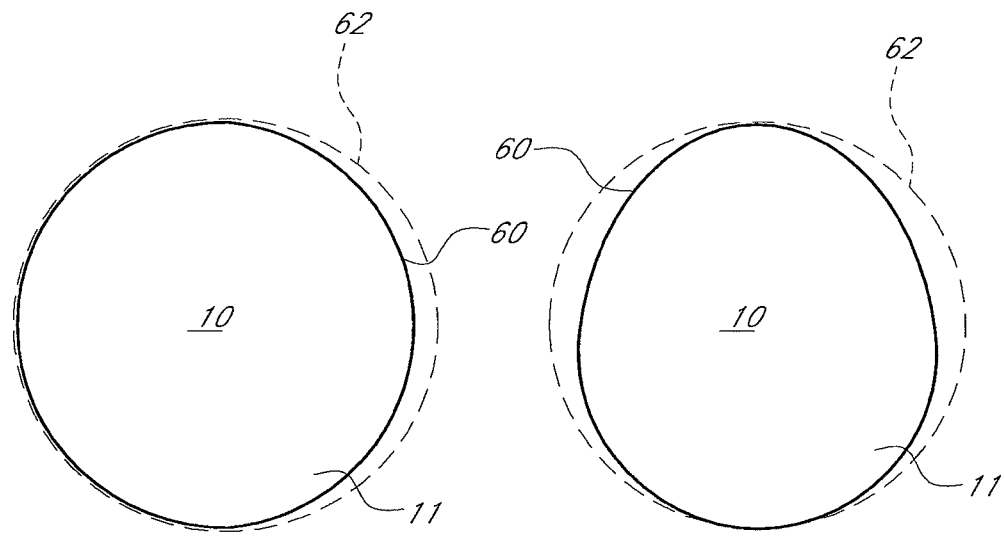
FIG. 9A is a top view of a head component illustrating a noncircular periphery of an embodiment compared to a circular periphery.
FIG. 9B is a top view of a head component illustrating a noncircular periphery of another embodiment compared to a circular periphery of the prior art head.

Referring now to the embodiment illustrated in FIG. 6, the top articulating surface 11 of the head component 10 can comprise a substantially convex surface that articulates with a mating bearing (not shown). The head 10 can have a bottom surface 53 and also comprise an attachment recess 52, such as a taper, opposite the articulating surface 11. The attachment recess 52 can be used to attach the head 10 to an intermediate or supportive substrate (not shown) of a bone using a coupling mechanism. Examples of head components 10 include, but are not limited to a humeral head (meaning the top of the long bone of the upper arm where it joins the shoulder), a femoral head (meaning the ball portion of a hip joint), a reverse glenosphere (the glenosphere is the ball portion of a shoulder joint; in a reversed prosthesis design, the forces in the joint are directed through the center of the glenosphere, converting the centrifugal (outward) forces into centripetal (inward) forces), a humeral resurfacing component (meaning the metal cap that replaces the natural humeral head surface, for example the Depuy Global Cap), and a femoral resurfacing component (meaning the metal cap that replaces the natural femoral head surface, for example, the Zimmer Durom Femoral Resurfacing). Examples of the coupling mechanism are tapers, screws, or locking mechanisms for fixation to another prosthetic component and pegs, keels, or screws for fixation to bone. It should also be appreciated that the recess 52 can be replaced or used with a projection member. In other embodiments, the head component 10 can be integrally formed with or permanently attached to the coupling mechanism.

According to various embodiments, the articulating surface 11 of the head 10 can be a generally convex surface with a curvature that continuously varies and/or varies over a large number of connecting radii. FIGS. 3, 5-5C and FIGS. 7-9B illustrate exemplary configurations of the articulating surface 11 of the head 10. In this regard, although the articulating surface 11 can be referred to as "convex," it is contemplated that the surface 11 can still include non-convexities, such as concavities or planar areas that deviate from a completely convex surface. In some embodiments, these variations may be applied locally, as shown by element 54 of the side view of FIG. 7. However, in other embodiments, such as that illustrated in the side view of FIG. 8, these variations can be applied across the entire surface, where element 56 indicates a spherical curve and element 58 illustrates a varied curvature of the head 10 that can include abrupt or gradual changes in curvature. Furthermore, it is contemplated, as illustrated in top views of the head 10 shown in FIGS. 9A and 9B, that the variable curvature can alter the shape of a periphery 60 of the head 10. Therefore, although the periphery 60 can, in some embodiments, conform to a circular footprint 62, the periphery 60 can be variously configured to conform to a variable or constant curve having abrupt or gradual changes in curvature. The variability of the surface 11 and the periphery 60 may be used to alter constraint, soft tissue tension, and moment or arc of motion as will be described below.

Figure 5:
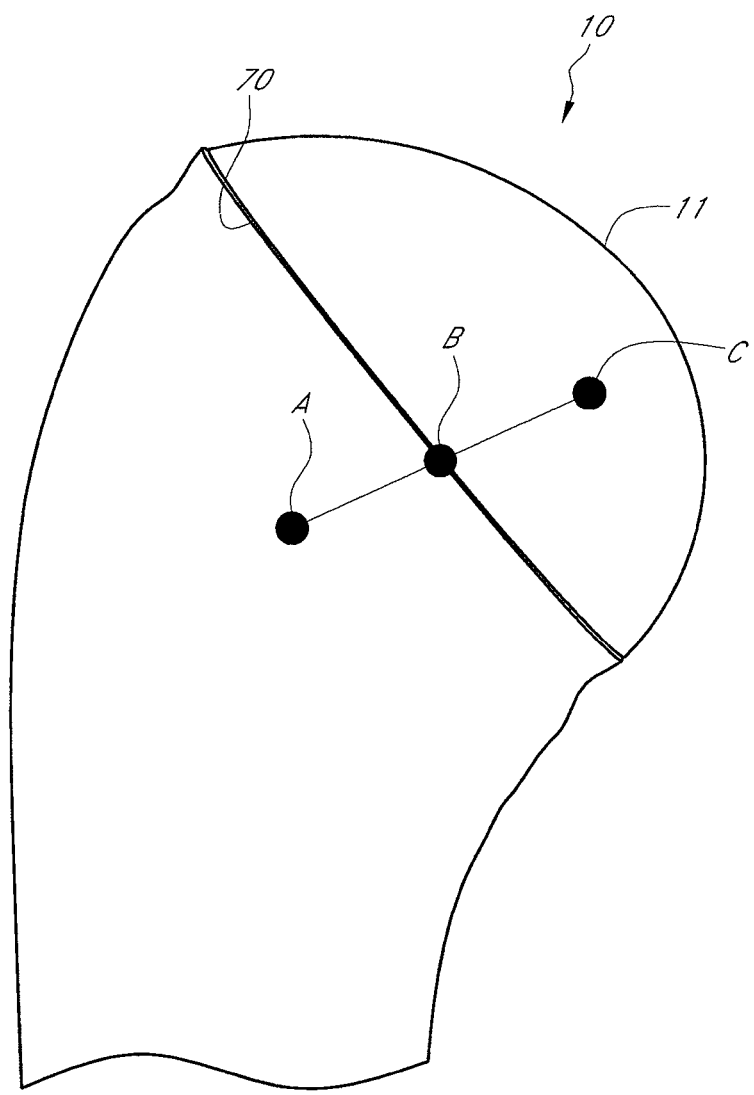
FIG. 5 is a side view of a head component positioned on a humerus.

With reference to FIGS. 3 and 5, in one preferred embodiment for the shoulder, the radius of the articulating surface 11 of the head gradually increases from a local minimum near the area of contact when the arm is in a neutral position. "Neutral position" as used herein is when the arm hanging down at the side of the subject is in a relaxed position. In one embodiment, the area of contact when the arm is in a neutral position forms a line extending to the center of curvature of the head 10. Depending upon the anatomy of the subject, the angle between the line and the supporting surface 70 of the humerus is between about 20 and 40 degrees and often about 30 degrees. FIG. 5 illustrates another advantage of the illustrated embodiment. As shown in this Figure, the center of rotation at the resting or neutral position is indicated by point labeled "B". The point labeled "A" is the center of rotation (at resting) of a standard spherical head while the point labeled "C" is the center of rotation (at resting) of a reverse prosthesis. As shown, the illustrated embodiment advantageously moves the center of rotation further away from where the force is applied (see FIG. 3). Accordingly, the illustrated non-spherical arrangement advantageously increases the moment of the arm which is one of the advantages of a reverse shoulder prosthesis.

Figure 5A:
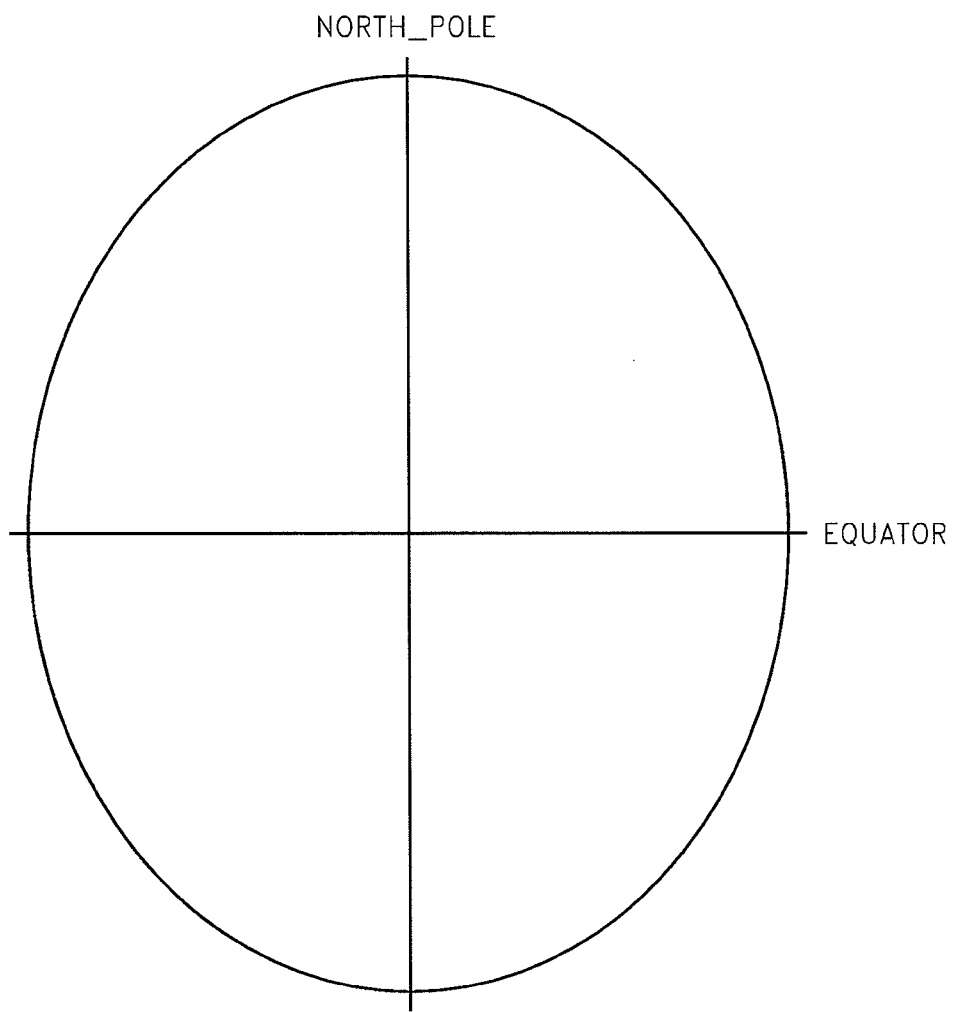
FIG. 5A is a side view of a spheroid.
Figure 5B:
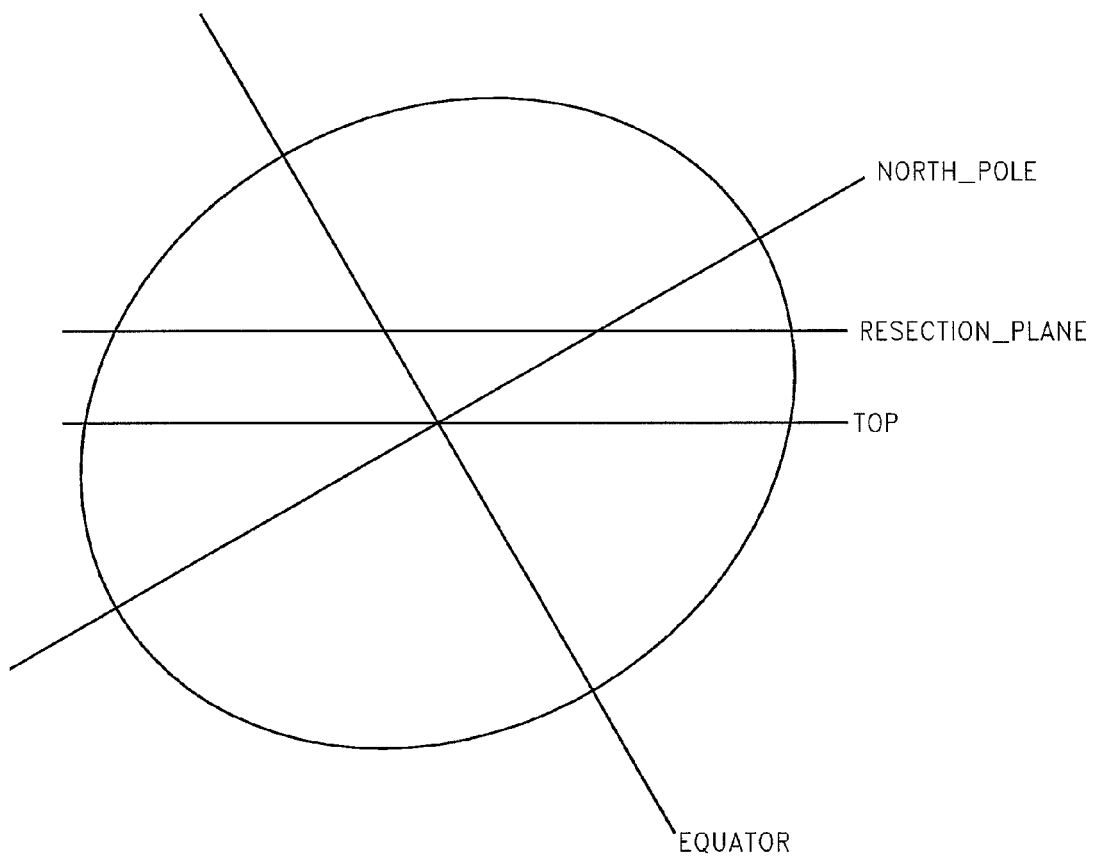
FIG. 5B is a side view of the spheroid of FIG. 5A rotated about its major axis.
Figure 5C:
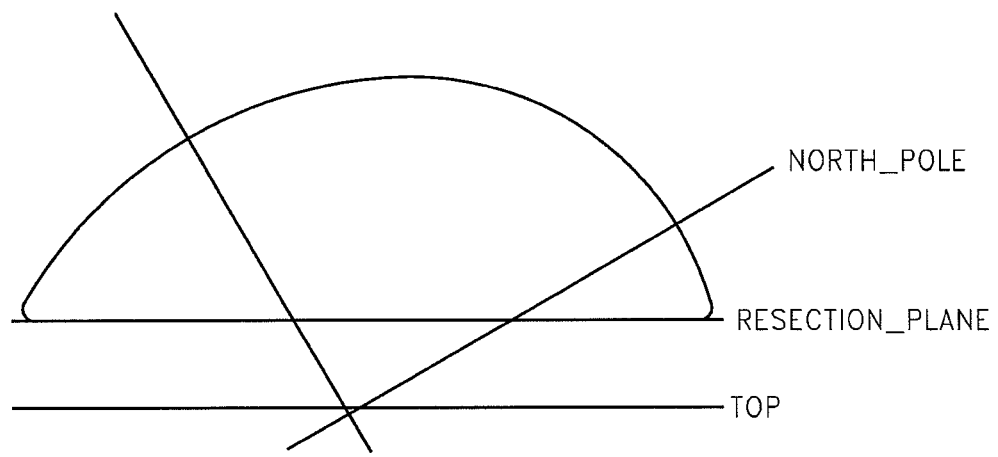
FIG. 5C is a side view of the spheroid of FIG. 5B resected by a plane.
Figure 5C:
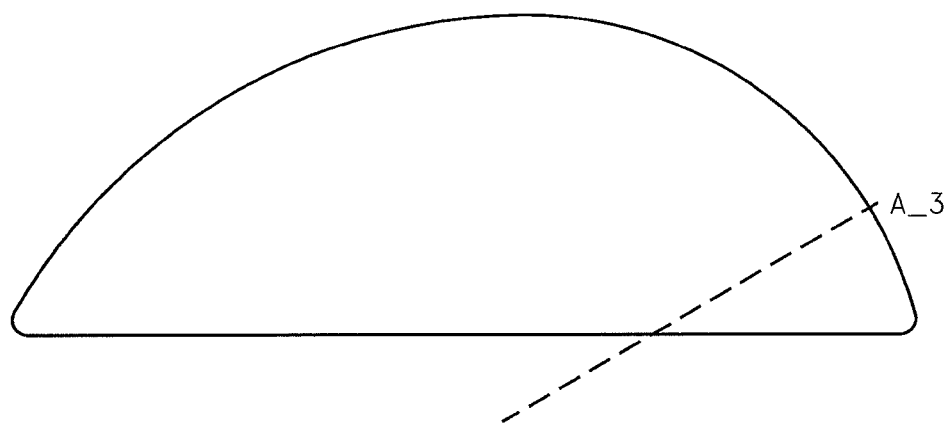

With reference now to FIGS. 5A-C, the shape of the head component 10 of FIGS. 3 and 5 described above will now be described in more detail. The shape of this embodiment of the head component 10 can be defined by initially referring to a shape that corresponds substantially to a Prolate spheroid as illustrated in FIG. 5A. A Prolate spheroid can be defined by the equation (1) instated below.

$$\frac{x^2+y^2}{a^2}+\frac{z^2}{c^2}=1 \qquad \text{Equation 1}$$

As shown in FIG. 5B, the spheroid can be rotated such that its major axis is tilted in one embodiment between about 40 and about 80 degrees and in another embodiment between about 50 and about 70 degrees and in another embodiment about 60 degrees. As shown, in FIG. 5C, the spheroid is then resected at a plane such that it represents between about 65% to about 85% of a semicircle and in another embodiment between about 70% and about 80% of a semicircle and in another embodiment about 75% of a semicircle. In resecting the spheroid, the referenced percent of a semicircle represents that the thickness is a specific percent of the radius of curvature of a spherical head of the same size as the spheroid. For example, if a spherical head was made of the same periphery diameter and thickness, the thickness would be a specific percentage of the spherical radius of curvature. As shown in FIG. 5C, this forms a humeral head with an axis of rotation that is at an angle of between about 40 degrees and about 80 degrees in one embodiment, to between about 50 and about 70 degrees in another embodiment to about 60 degrees in another embodiment. One advantage to this arrangement is that it advantageously moves the center of rotation further away from where the force is applied (see FIG. 3) and increases the moment of the arm.

As discussed above, the head 10 and the bearing 12 can each be utilized with a corresponding "intermediate substrate" which, in turn, is coupled to a "supportive substrate." The term "intermediate substrate" as used herein refers to a support that bears or holds up the weight, pressure, strain, and the like of the head components 10 or bearing components 12. The term "supportive substrate" as used herein refers to a surface of the subject that bears or holds up the weight, pressure, strain, and the like of the intermediate support and thus, in turn, head components 10 or bearing components 12. Thus, in one embodiment, the intermediate substrate can be another implant to which the head component 10 or the bearing component 12 can be integrally formed with, permanently attached or coupled to. An example of a corresponding intermediate substrate 70 for the head component 10 (a humeral head component) can include, but is not limited to, a humeral stem (not shown), which is configured to be positioned within the humerus. Likewise, an example of the corresponding intermediate substrate 70 for a femoral head component includes, but is not limited to, a femoral stem (not shown). The intermediate substrate, in turn, is typically coupled or attached to a supportive substrate. In most cases, the supportive substrate is a portion of the subject's bone. For example, the humerus typically supports a humeral stem while the femur would support a femoral stem.

Thus, as used herein, the term "stem" can refer to a device that is implanted into the bone for the purpose of supporting a functional component of the joint replacement and resisting the loads applied to the functional component. For example a stem may be implanted into a humerus or femur to support a modular prosthetic humeral or femoral head. The supported structure may also be an integral part of the stem, as with a monolithic stem and head. Femoral and humeral stems typically include distal and proximal seconds as well as a taper or other coupling device to which the functional component is attached. Additionally, femoral stems typically include a neck section that extends the distance between the proximal section and the head. The neck is not embedded in the bone, but sits proud. As used herein, the term "neck" refers to the portion of a femoral stem that does not reside within the femur bone, and extends the distance between the proximal body and the head. Additional details and embodiments of stems that can be utilized with the head components 10 described herein can be found in co-pending U.S. patent application Ser. No. 11/689,470, filed Mar. 21, 2007, which claims the priority benefit of U.S. Provisional Application 60/784,236, filed on Mar. 21, 2006, the entirety of these applications are hereby incorporated by reference herein.

Figure 10:
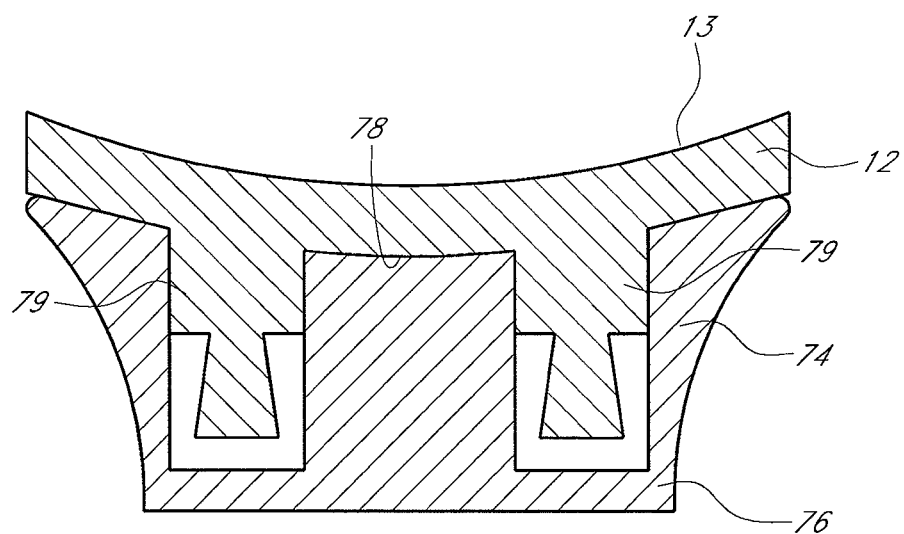
FIG. 10 is a side cross-sectional view of the bearing component and a supportive substrate, according to an embodiment.

Similarly, as shown in the side view of FIG. 10, the bearing component 12 can be attached to a supportive substrate 74. An example of the corresponding supportive substrate 74 for a glenoid resurfacing component or bearing component 12 includes, but is not limited to the glenoid bone 76. In this embodiment, the intermediate substrate is formed by the lower surface 78 of the bearing component 12 itself. An example of an intermediate substrate 74 for a reverse glenoid component includes, but is not limited to, a glenosphere base plate, such as the Tornier Aequalis Reversed Shoulder G2 Baseplate, or a glenoid bone. An example of a supportive substrate of a reverse humeral bearing includes, but is not limited to, a reverse humeral stem, such as the Tornier Aequalis Reverse Humeral Stem. An example of a supportive substrate 74 for a humeral resurfacing component or bearing component 12 includes, but is not limited to, a humeral bone. An example of a supportive substrate 74 for a femoral resurfacing component or bearing component 12 includes, but is not limited to a femoral bone. An example of an intermediate substrate for an acetabular bearing or bearing component 12 includes, but is not limited to an acetabular cup such as the DePuy Pinnacle Acetabular Shell.

According to the embodiment illustrated in FIG. 10, the upper articulating surface 13 of the bearing component 12 can be substantially concave and be configured to articulate with a mating surface, a convex surface, or a flat surface of a head component 10. As shown, the bearing component 12 can include a lower surface 78 that rests on the supportive substrate 74. Further, the bearing component 12 can include at least one fixation mechanism 79. Examples of such a bearing component 12 include, but are not limited to glenoid resurfacing components such as the Tornier Aequalis Glenoid, reverse humeral bearings such as the Tornier Aequalis Reversed Shoulder Polyethylene Insert and acetabular bearings such as the Depuy Marathon Polyethylene Liner.

Referring still to FIG. 10, the fixation mechanism 79 is configured to hold or retain the bearing component 12 in position relative to the supportive substrate 74. The fixation mechanism 79 can be variously configured; however, in a preferred embodiment, the fixation mechanism 79 can protrude or extend from the rear surface 78. Additional details of the illustrated fixation mechanism can be found in copending U.S. patent application Ser. No. 11/689,424, filed Mar. 21, 2007, which claims the priority benefit of U.S. Provisional Application No. 60/784,237, filed Mar. 21, 2006, the entirety of these applications are hereby incorporated by reference herein. Another example of a fixation mechanism 79 for a glenoid resurfacing bearing component and a glenoid bone supportive substrate includes, but is not limited to, a cemented glenoid peg, such as the Tornier Aequalis pegged glenoid. An example of a fixation mechanism 79 for a reverse humeral bearing component and a reverse humeral stem supportive substrate includes, but is not limited to, a locking mechanism in the reverse humeral stem, such as the Tornier Aequalis reverse humeral stem. An example of a fixation mechanism 79 for an acetabular bearing component and an acetabular cup intermediate substrate includes, but is not limited to, a locking mechanism in the acetabular cup as the DePuy Pinnacle Acetabular Shell.

In addition, it is also noted that the term "substantially concave" as used herein can refer to a surface that is concave to a great extent or degree, but not completely concave. Local convexities or planar areas can exist, but preferably most of the edge or more preferably substantially all of the edge should be higher than the lowest spot, and the slope should not become negative with respect to the sagittal plane.

Figure 11:
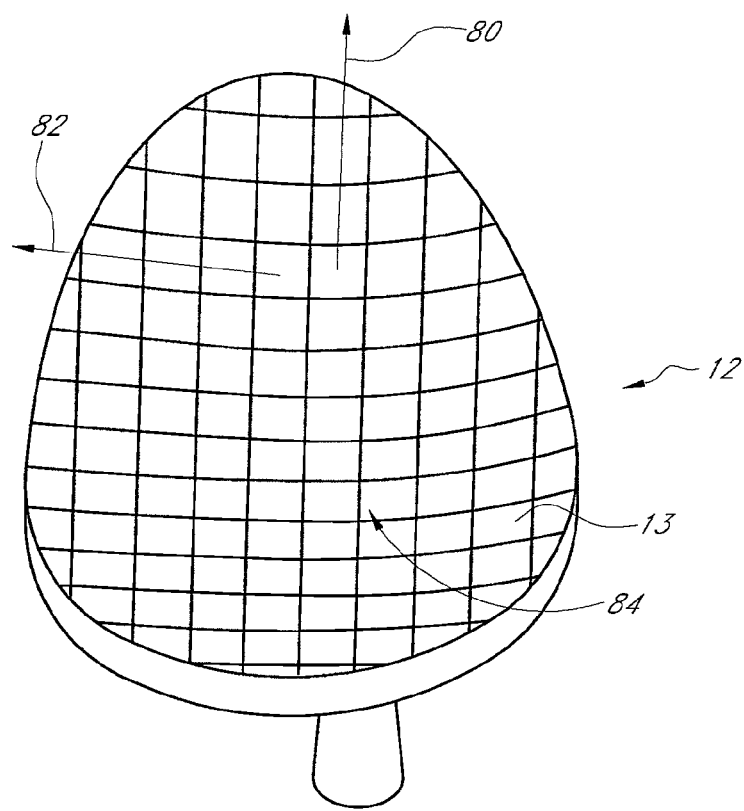
FIG. 11 is a perspective view of an embodiment of the bearing component having a fully concave variable curvature articulating surface.
Figure 12:
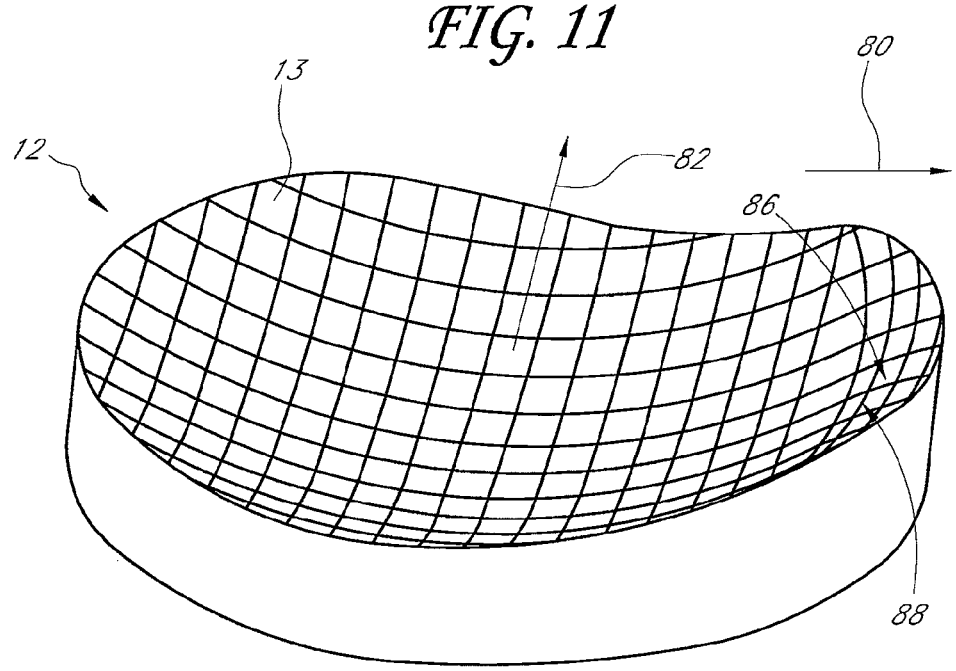
FIG. 12 is a perspective view of another embodiment of the bearing component illustrating local and directional convex curvature applied thereto.

For example, as shown in FIGS. 11-14, the articulating surface 13 of the bearing component 12 can be configured to be fully concave, to have a variable curvature, or to have local convex curvatures. As shown in FIG. 11, the surface 13 can be fully concave with regions of varying curvature. Such variations in curvature can allow the surface 13 to maintain its concavity in longitudinal and transverse directions 80, 82 while having varying degrees of concavity. Therefore, in an embodiment, local curvatures can be convex in both directions, as indicated by area 84. In another embodiment shown in FIG. 12, local curvatures can be convex in the longitudinal direction 80 and concave in the transverse direction 82, as indicated by area 86. Further, yet another embodiment can be configured with local curvatures that are convex in the transverse direction 82 and linear in the longitudinal direction 80.

In a preferred embodiment, shown in FIG. 13, a periphery 90 of the bearing component 12 can be configured to include a local curvature that is convex in both the longitudinal and transverse directions 80, 82. Such local convex curvature can be applied around the entire periphery 90 or only in segments of the periphery 90 where they are required. Furthermore, this local convex curvature about the periphery 90 can be applied evenly and consistently, as shown in FIG. 14A. As shown there, the local convex curvature can be applied along a peripheral border 92 having an approximately constant width. However, as shown in FIG. 14B, the local convex curvature can be applied along a peripheral border 92' having a variable width. As such, the local convex curvature can vary in size and curvature. Finally, it is contemplated that any of the features and embodiments discussed herein can be combined or modified such that the variable curvature of the articulating surface 13 in both the longitudinal and transverse directions 80, 82 can be used to alter constraint, soft tissue tension or moment or arc of motion.

Figure 15:
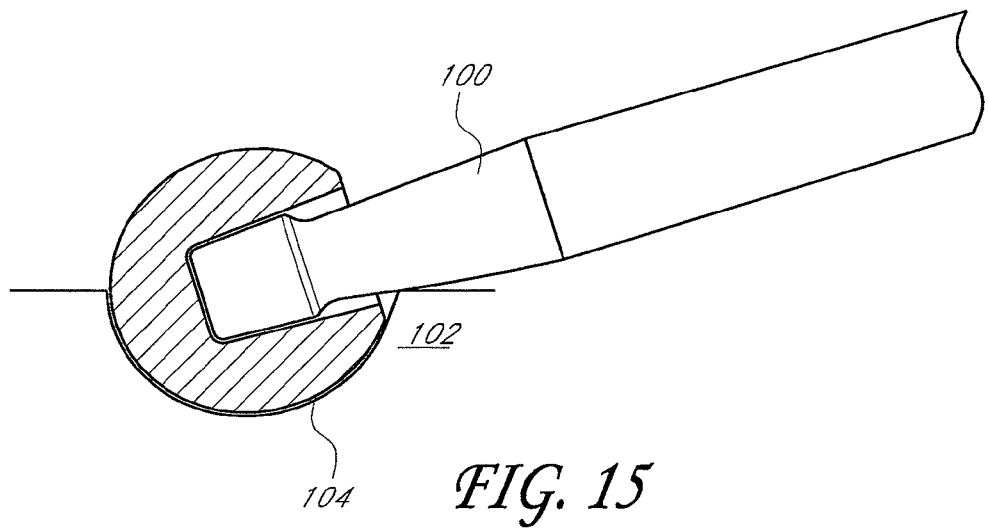
FIG. 15 is an illustration of a neck of a hip stem impinging on an acetabular bearing.
Figure 16:
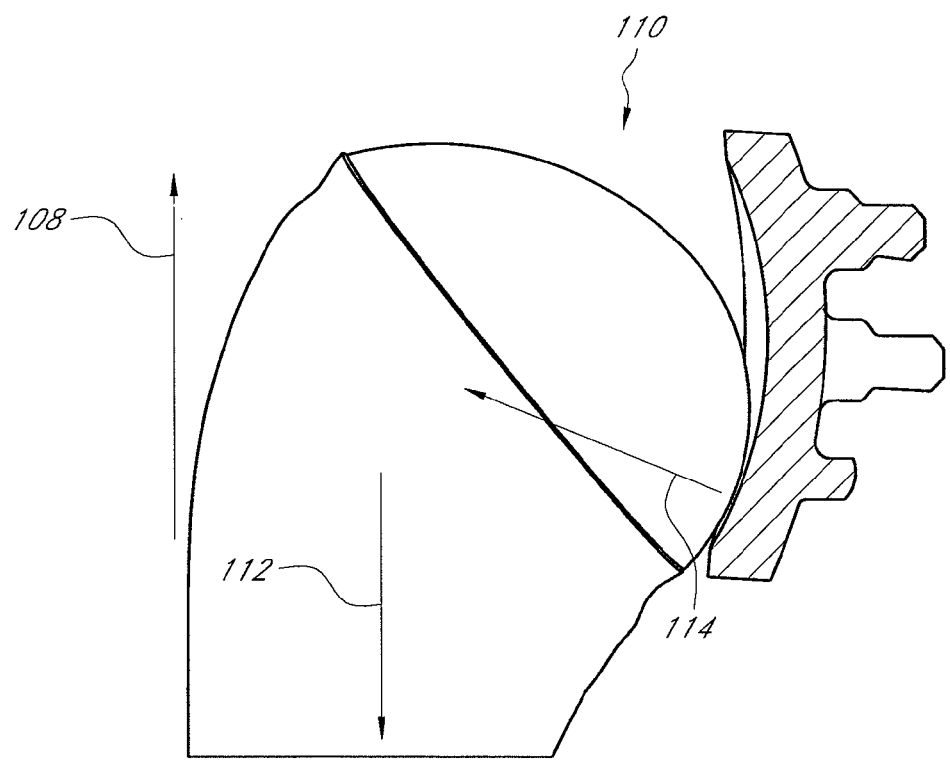
FIG. 16 is an illustration of the balance between muscle force, arm weight, and joint reaction force.

As described above, the ability of a prosthesis to provide a range of motion comparable to a normal joint is restricted by multiple factors. Three factors in particular can limit the range of motion, as illustrated in FIGS. 15-17. One of these factors, "impingement," is illustrated in FIG. 15 and refers to a situation in which one body (such as a femoral stem neck 100) contacts another body (such as an acetabular bearing 102) outside of an intended articulating surface 104. The bodies can be either implants or natural structures such as bone or ligaments. Another factor, shown in FIG. 16, is "insufficient muscle efficiency." Insufficient muscle efficiently refers to a situation that occurs when a force 108 or moment that muscle(s) can apply is less than what is required to flex a joint 110 against an arm weight 112 and a joint reaction force 114. Yet another factor is the angle of the arc of motion illustrated in FIG. 17; the angle of an arc of motion is termed too small when the point of contact simply comes to the end of the articulating surface before the desired flexion is reached. Each of these factors is described in greater detail below.

The variables conformity, slope, instantaneous center of curvature, arc of motion, and part thickness are available for direct modification using non-spherical articulating surfaces. In turn, each of these variables interrelates with each of the other variables and effect impingement and muscle/resistive force balance either directly or indirectly. The variable that most directly affects impingement is part thickness. Therefore, at least in theory, impingement can be reduced by increasing the thickness of a related part. For example, as shown in FIGS. 18A-B, the impingement of a femoral stem neck on an acetabular cup can be alleviated by increasing a local thickness of a femoral head. The local thickness of the femoral head can be increased by using non-spherical geometry, instead of spherical geometry, for the femoral head. Thus, as shown in FIG. 18A, a femoral stem neck 120 impinges on an acetabular cup 122 due to insufficient local thickness 124 resulting from the spherical geometry of a femoral head 126. In contrast, where the head geometry is non-spherical, as illustrated in FIG. 18B, local thickness 130 of a femoral head 132 can be increased relative to that shown in FIG. 18A, thereby increasing the angle at which impingement of a femoral stem neck 134 on an acetabular cup 136 occurs. As a result, greater range (arc of motion is a measure of geometry of a single part, range of motion is a measure of the available motion of two or more articulating parts) of motion is achieved. This means that a non-spherical curvature on the head component 132 can be used to increase the distance from a head center 138 to the point of contact with the acetabular bearing in a position that would precede the contact point at impingement. The femoral stem 134 can be moved away from the cup 136 by increasing the distance between the femoral head 132 and the cup 136 to mitigate the likelihood of impingement.

Figure 19:
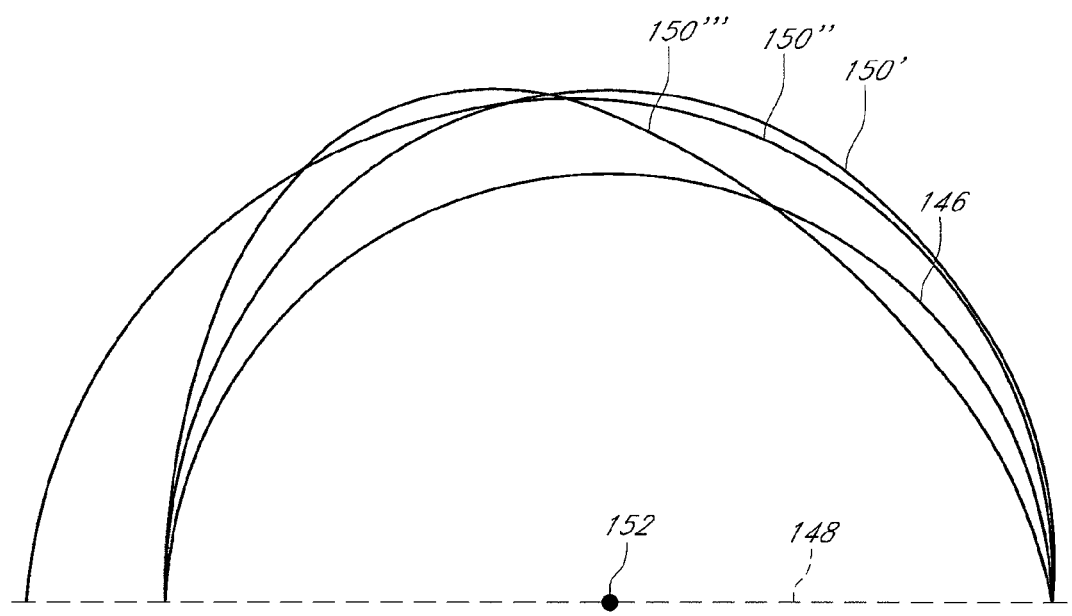
FIG. 19 shows a comparison of circular and non-circular femoral head curves, according to an embodiment.

The following embodiment is an example of how this geometry could be created. However, those of skill in the art will recognize other methods for creating the geometry and/or other environments in which the geometry can be used. Referring to FIG. 19, if the geometry for a spherical head is created by revolving a semi-circle 146 about an axis 148, the geometry for a type of head for increasing local thickness could be created by revolving a non-circular curve 150', 150", or 150''' about the axis 148. The curves 150', 150", or 150''' themselves could be created using multiple radii or complex, continuously varying curves such as those created with polynomials, trigonometric, or exponential functions. For example, the starting point of the curve 150', 150", or 150''' could be the same as the semi-circle 146 corresponding to the spherical head. The distance from any point on this curve to a spherical head center 152 could gradually increase as the position approached the point corresponding to the point of contact at impingement. The distance from the spherical head center 152 to the curve 150', 150", or 150''' could continue increasing to the end of the articulating surface, or it could begin to decrease after a certain point.

Figure 20:
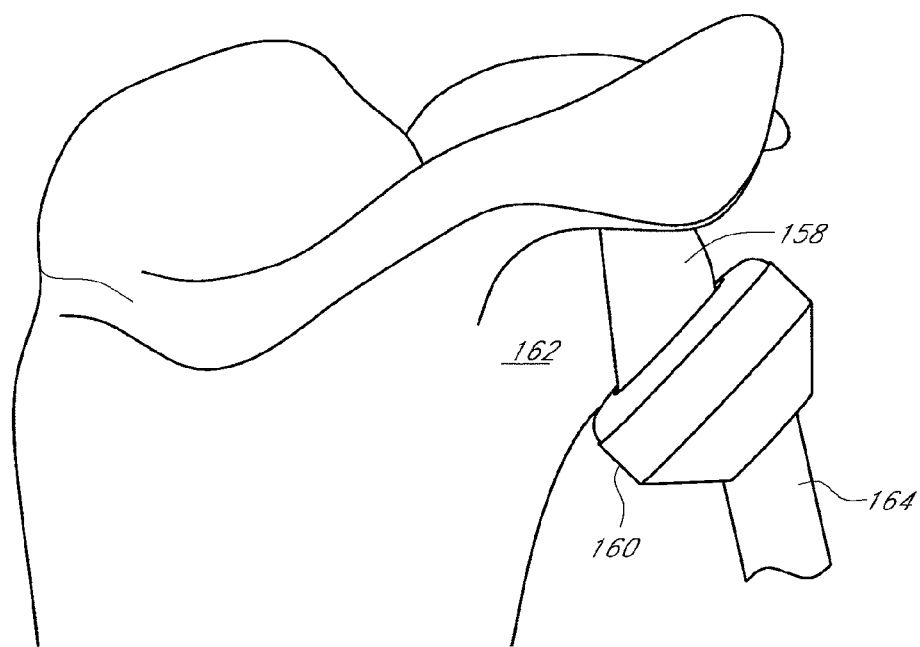
FIG. 20 shows an illustration of scapular notching of a reverse bearing due to spherical glenoid shape.
Figure 21:
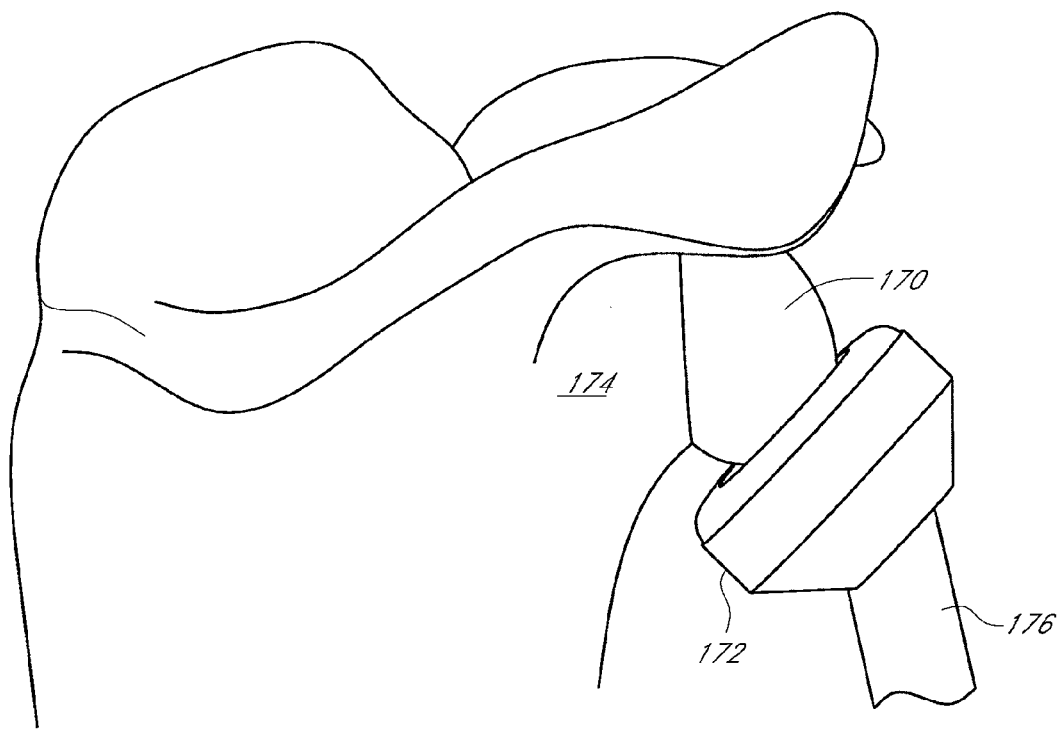
FIG. 21 shows how a non-spherical glenoid can eliminate scapular notching, according to an embodiment.

Likewise, increasing part thickness can be used for a glenosphere of a reverse shoulder. Referring now to the illustration of FIG. 20, with a spherical glenosphere 158, scapular notching is a common problem that occurs when a reverse humeral bearing 160 impinges on a scapula 162 when the stem 164 is near a neutral position. However, the shape of the glenosphere 158 can be changed from the spherical to increase joint thickness in a neutral position. Such an embodiment is illustrated in FIG. 21, where a non-spherical glenosphere 170 is configured to eliminate impingement of a reverse humeral bearing 172 on a scapula 174 and move the humerus 176 away from the scapula 174.

The following embodiment is an example of how this geometry could be created. However, those of skill in the art will recognize other methods for creating the geometry and/or other environments in which the geometry can be used. If the geometry for a spherical glenosphere is made by creating three circular cross sections at 90 degrees from each other, and blending from one to another to create a hemispherical surface, the nonspherical glenosphere surface could be created by replacing one or more of these spherical curves with non spherical curves. For this particular example, the second curve, corresponding to the sagittal plane could be made non-spherical so that the distance from the curve to the spherical center was gradually increased in the lateral/inferior area, as similarly discussed above with reference to FIG. 19. This would move the apex of the head and in turn move the neutral position of the reverse bearing further away from the scapula. Other shapes could be created by using more than three curves and/or by varying more than one curve. The curves themselves could be created using multiple radii or complex, continuously varying curves such as those created with polynomials, trigonometric, or exponential functions.

Figure 22:
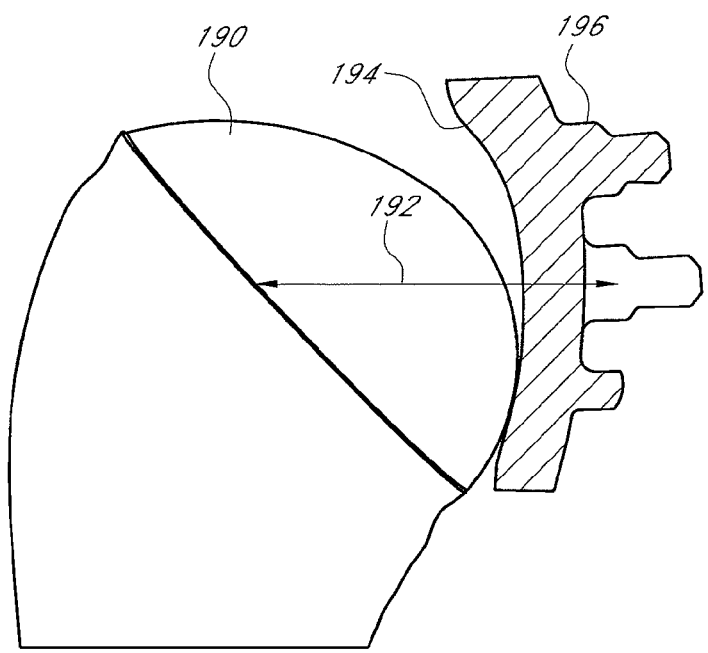
FIG. 22 shows how non-spherical surfaces can be used to increase joint thickness and superior constraint, according to an embodiment.

Similarly, increasing part thickness can be used to limit impingement due to superior migration with a standard shoulder. "Superior migration" occurs when the force required to translate the humerus superior is less than the force required to flex the joint. If superior translation is enough, the humerus and surrounding rotator cuff impinge on the acromion. As shown in the side view of FIG. 22, the shape of a humeral head 190 can be modified from a spherical shape to increase joint thickness 192 in a neutral position as described above. This would increase soft tissue tension which would increase constraint and help hold the humerus inferior. As shown in FIG. 22, a slope 194 of a glenoid surface 196 can be locally increased to further add constraint.

Figure 23:
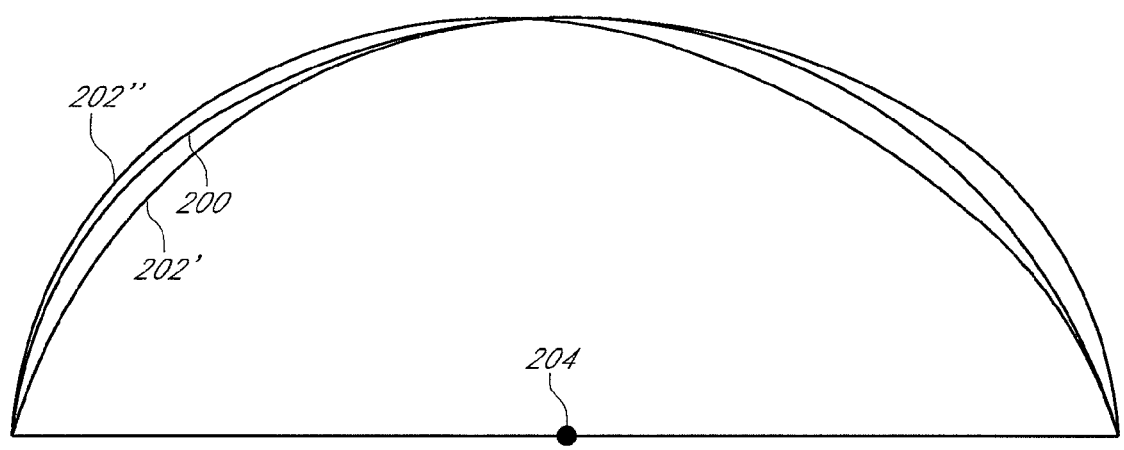
FIG. 23 shows a comparison of circular and noncircular curves used to create a spherical or non-spherical humeral head, according to an embodiment.
Figure 25:
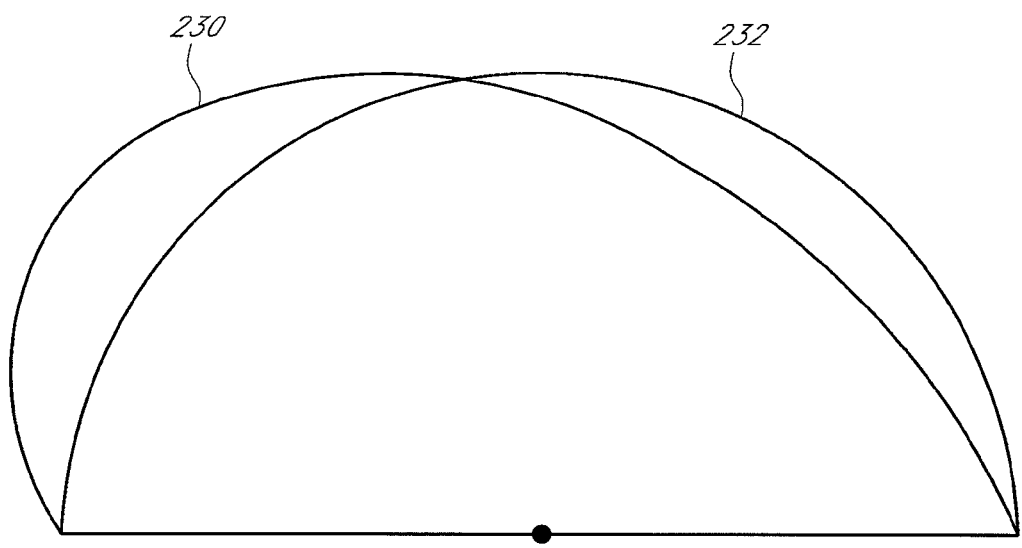
FIG. 25 shows a comparison of circular and noncircular curves that can be used to create a spherical or non-spherical glenosphere.

With respect to the head 190, the following embodiment is an example of how this geometry could be created. However, those of skill in the art will recognize other methods for creating the geometry and/or other environments in which the geometry can be used. If the geometry for a spherical humeral head is made by creating three circular cross sections at 90 degrees from each other, and blending from one to another to create a partial spherical surface, the non-spherical humeral head surface could be created by replacing one or more of these circular curves with non-circular curves. For this particular example, the second curve, which is represented in FIG. 23 and corresponds to the coronal plane, could be made non-spherical. Thus, instead of a circular curve 200, the second curve could be configured as a non-circular curve 202' or 202" so that the distance from the curve 202' or 202" to a spherical center 204 is gradually increased in the medial/inferior area. This would move the apex of the head and in turn move the neutral position of the humerus further away from the scapula, in doing so, increasing soft tissue tension in the neutral position. The curves themselves could be created using multiple radii or complex, continuously varying curves such as those created with polynomials, trigonometric, or exponential functions. An exaggerated example of such a curve can be seen in FIG. 25, where the reference number 232 represents the spherical curve and reference number 230 represents the non-spherical curve. Other shapes could be created by using more than three curves and/or by varying more than one curve.

Insufficient muscle efficiency is, by far, the most complex of the three limitation factors. It can occur either when the forces restricting motion exceed the force that the muscles can exert or when the force to induce flexion (i.e., bending a joint) is more than the force to induce translation. Apart from muscle weakness, insufficient muscle efficiency can be caused by excessive soft tissue tension or insufficient muscle moment arm. Generally more of a problem in shoulder prostheses than in hip prostheses, it can also occur when there is insufficient soft tissue constraint in the shoulder, causing the humerus to translate instead of flex. This cause can be corrected by adding implant constraint and increasing moment arm.

Figure 24:
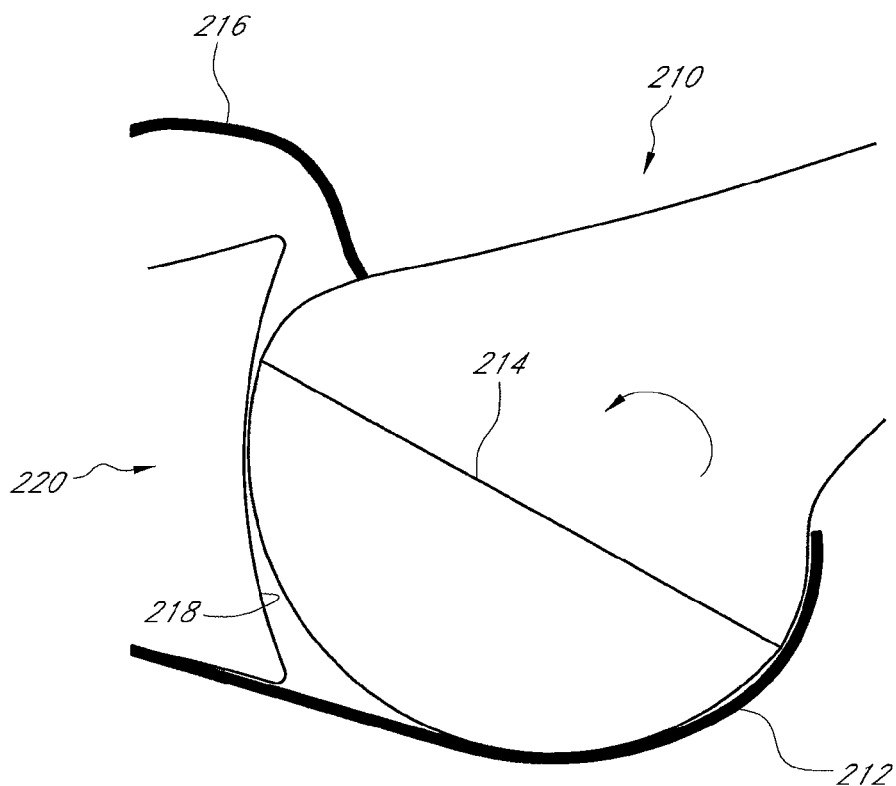
FIG. 24 shows how soft tissue must wrap around the head in flexion.

The shoulder joint is surrounded by the rotator cuff as well as other various ligaments, muscles and tendons. As the joint flexes, pivots, rotates, or slides, the tension in the soft tissue increases or decreases in opposition to this motion. If any part of this surrounding tissue gets too tight, it will restrict flexion or impart translation. Referring to FIG. 24, during flexion and rotation of a joint 210, the tension of soft tissue 212 on one side of a humeral head 214 will increase while tension of soft tissue 216 on the other side will decrease. Translation of the humeral head 214 along surface 218 of glenoid 220 may be required in conjunction with flexion or rotation to minimize the tension of the soft tissue 212 and to maximize range of motion.

For this reason, during certain activities, when rotation or flexion is expected, more translation in a certain direction may be beneficial. In such a case, a non-spherical articulating surface on the humeral head 214 or on the glenoid 220 can be used to locally decrease conformity allowing more translation and better soft tissue balance. The shape to be used on the humeral head 214 could be created using the previously described method.

Using the same geometry described above, and with reference to FIGS. 23 and 25, the area of smaller radius on curves 230 and 202", would provide an area of decreased conformity with the glenoid while the areas of larger radius on the same curves would increase conformity with the glenoid.

The following embodiment is an example of how the glenoid geometry could be created. It is not the only method nor is it the only geometry to which this technology could be applied. In one embodiment, a spherical articulating surface could be created by blending eight radial curves in the superior, superior/anterior, anterior, inferior/anterior, inferior, inferior/posterior, posterior, and superior posterior directions on the glenoid. For a spherical surface, these curves would all be of equivalent radius, which would be the radius of the resulting surface. Similarly, the geometry for the non-spherical surface could be created using the same method, but by varying the curvature of one or more of the curves (FIG. 26B). For example, as shown in FIG. 26B, if more translation is required in the superior/anterior direction, the radius of a curve XYZ in that direction could be relaxed compared to a circular curve. The curves could also be complex curves that are made of several radii or a gradual progression of increasing or decreasing curvature. These types of curves could be used to customize the constraint at a particular radial position in any given direction. Any number of these curves could be varied from the circular to increase or decrease constraint in any desired direction. The number of curves used is not limited to eight: less than eight or more than eight curves also can be used to create the glenoid surface.

Figure 26A:
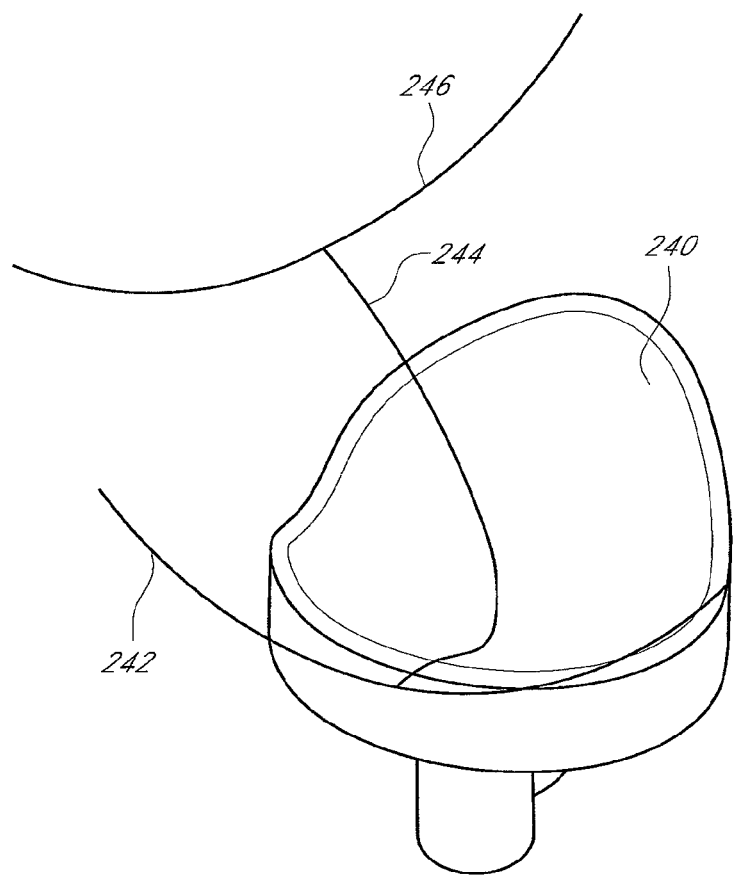
FIG. 26A is a perspective view of an articulating surface of the bearing component created by sweeping one curve along another, according to an embodiment.
Figure 26B:
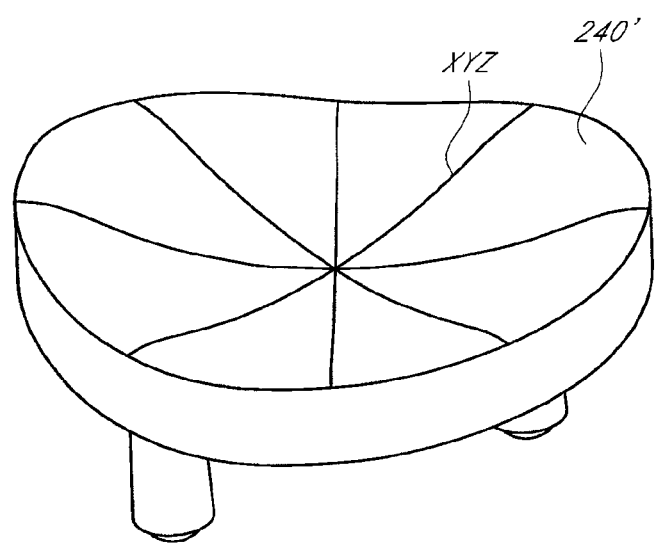
FIG. 26B is a perspective view of another articulating surface of the bearing component created by blending multiple radial curves, according to another embodiment.

Similarly, in another embodiment illustrated in FIG. 26A, if a spherical articulating surface is created by sweeping a planar curve of a specified radius normal to and along a second planar curve of the same radius, a non-spherical glenoid articulating surface 240 could be created by sweeping a first planar curve 242 normal to and along a second planar or three-dimensional curve 244. One or both curves 242, 244 could be composed of multiple radii or of continuously varying curvature. For example, in one embodiment, if more translation is desired in the superior/anterior direction, the first curve 242 could be a circular, multi-radii, or continuously variable planar curve, while the second is a three-dimensional curve 244 that is concave in the superior/inferior direction, but also curves in the anterior direction. Further, another curve 246 can be used and blended into the other curves 242, 244 to create the surface 240. Furthermore, it is contemplated that numerous curves can be blended to form the articulating surface. For example, FIG. 26B illustrates that an articulating surface 240' of a bearing component can be created by blending eight radial curves. Other embodiments and configurations can be created using the teachings herein.

Figure 27:
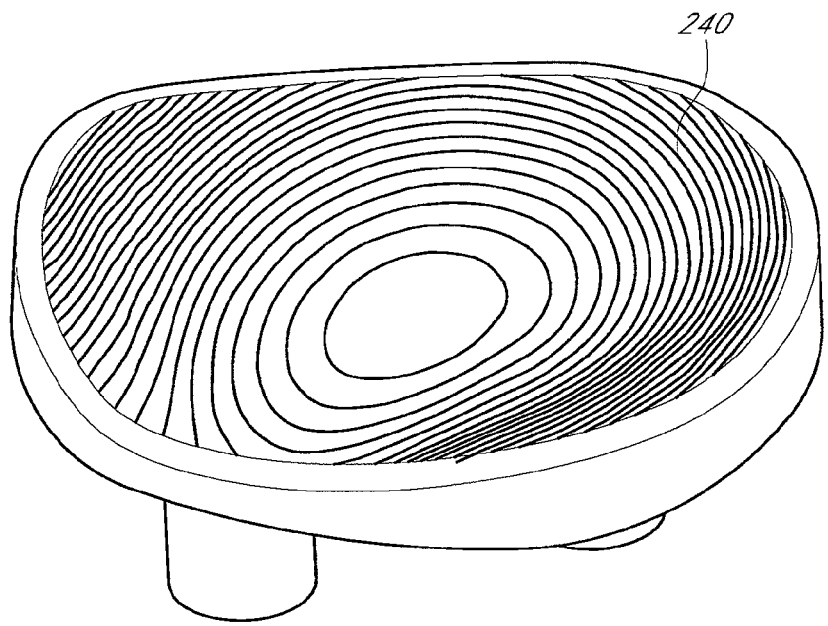
FIG. 27 shows how a non-spherical articulating surface of the bearing component can be used to decrease local conformity and allow more head translation, according to an embodiment.

In yet another embodiment, illustrated in FIG. 26A, the previously explained method also can be used with two or more swept curves. In this case the first curve 242 could be swept along and normal to the second curve 244 and the shape of this first curve would be gradually modified as it was swept, to achieve a final shape 246 at the end of the sweep. Similarly, the slope of the glenoid can be decreased locally to allow more translation or the thickness of the glenoid can be decreased locally to reduce joint thickness and alleviate tension. The geometry for these situations could be made in the same manner as previously described. FIG. 27 provides a perspective view of the resulting geometry.

Figure 28:
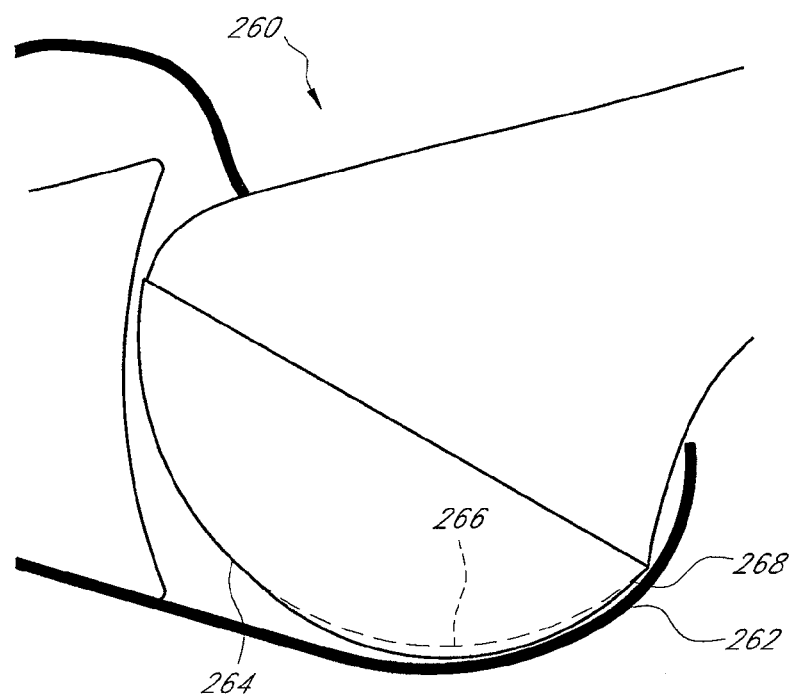
FIG. 28 shows how a non-spherical head component can reduce the distance that soft tissue has to wrap, according to an embodiment.

The shape of the features around which the soft tissue must wrap is another factor that affects soft tissue tension. This principle is illustrated in the exemplary illustration of FIG. 28. As a shoulder joint 260 flexes, for example, soft tissue 262 on the tight side must wrap around a humeral head 264. A flatter profile 266 in this area of the humeral head 264 would reduce the distance of this wrap and lessen soft tissue tension as compared to requiring the soft tissue 262 to wrap around a normal pronounced convex profile 268.

Figure 29:
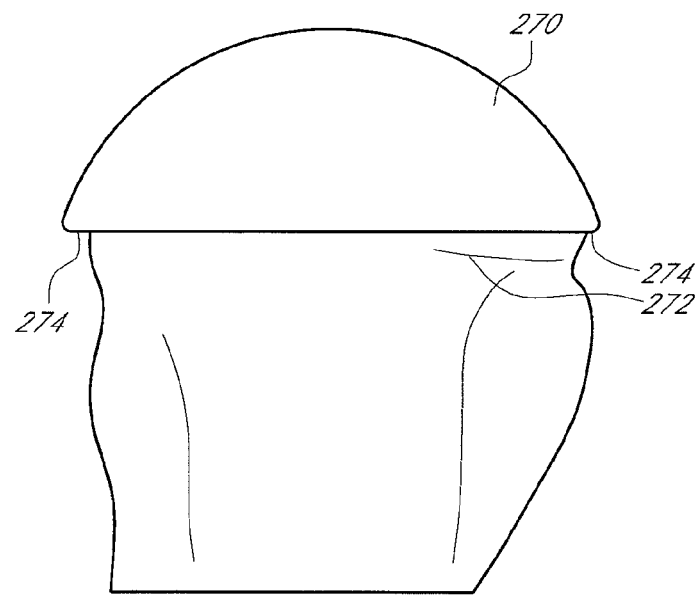
FIG. 29 shows overhang of a prior art spherical head when attached to a bone.

Similarly, as shown in FIG. 29, if the periphery of a humeral head 270 does not match the periphery of a resected head 272, the soft tissue will have the wrap further than normal to accommodate the protrusion of an edge 274 of the head 270. The geometry for this example could be created using the method of creating humeral head geometry, as described above with reference to FIGS. 23 and 25. In this case, however a possible desired curve shape for the sagittal curve would preferably have a more relaxed curvature in the superior/medial part of the curve for a humeral head or superior/lateral part of the curve for a glenosphere.

Figures 30A, 30B:
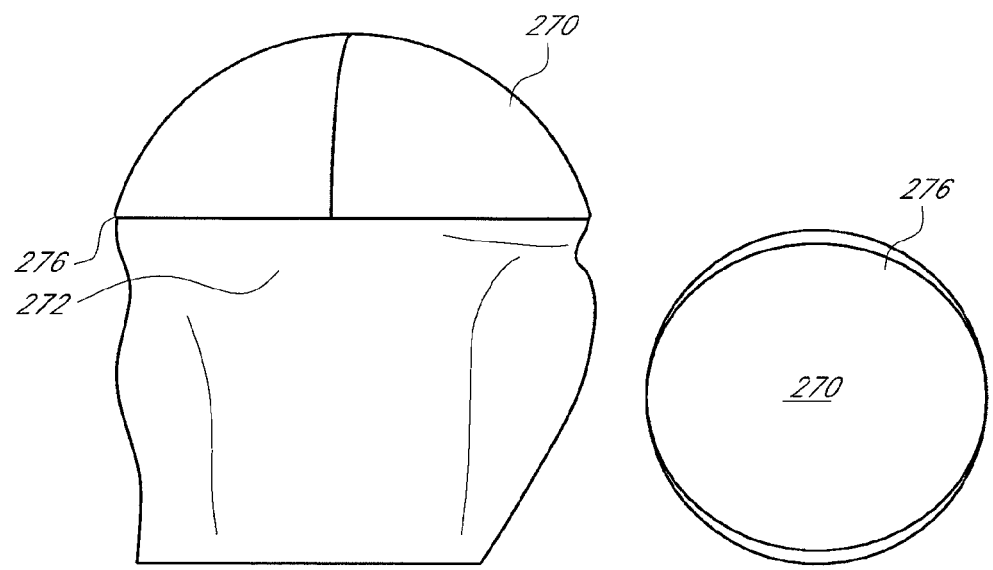
FIG. 30A is a side view of an embodiment of a non-spherical head component that is configured to reduce head overhang.
FIG. 30B is a top view of the non-spherical head component of FIG. 30A illustrating that head overhang can be reduced using a non-circular periphery, according to an embodiment.

Therefore, in some embodiments as illustrated in FIGS. 30A-B, a complex, non-spherical articulating surface on the humeral head 270 can be used to change the shape of a periphery 276 of the head 270 to better match the resected head 270. To better match the resected bone surface shape, and reduce the soft tissue wrap distance due to head or glenosphere overhang, one or both of the periphery curves could also be modified to reduce their overall anterior-posterior dimension in comparison to a circular periphery, as described above with reference to FIGS. 23 and 25.

Generally, the term "curvature" refers to the amount by which a geometric object deviates from being flat. In the context of an implant, curvature of a non-spherical surface may be described with respect to a nominal spherical reference. The term "radius of curvature" refers to the radius (the length of a line segment between the center and circumference of a circle or sphere) of the circle of curvature. Mathematically, it is equal to the absolute value of the reciprocal of the curvature of a curve at a given point.

Figure 31:
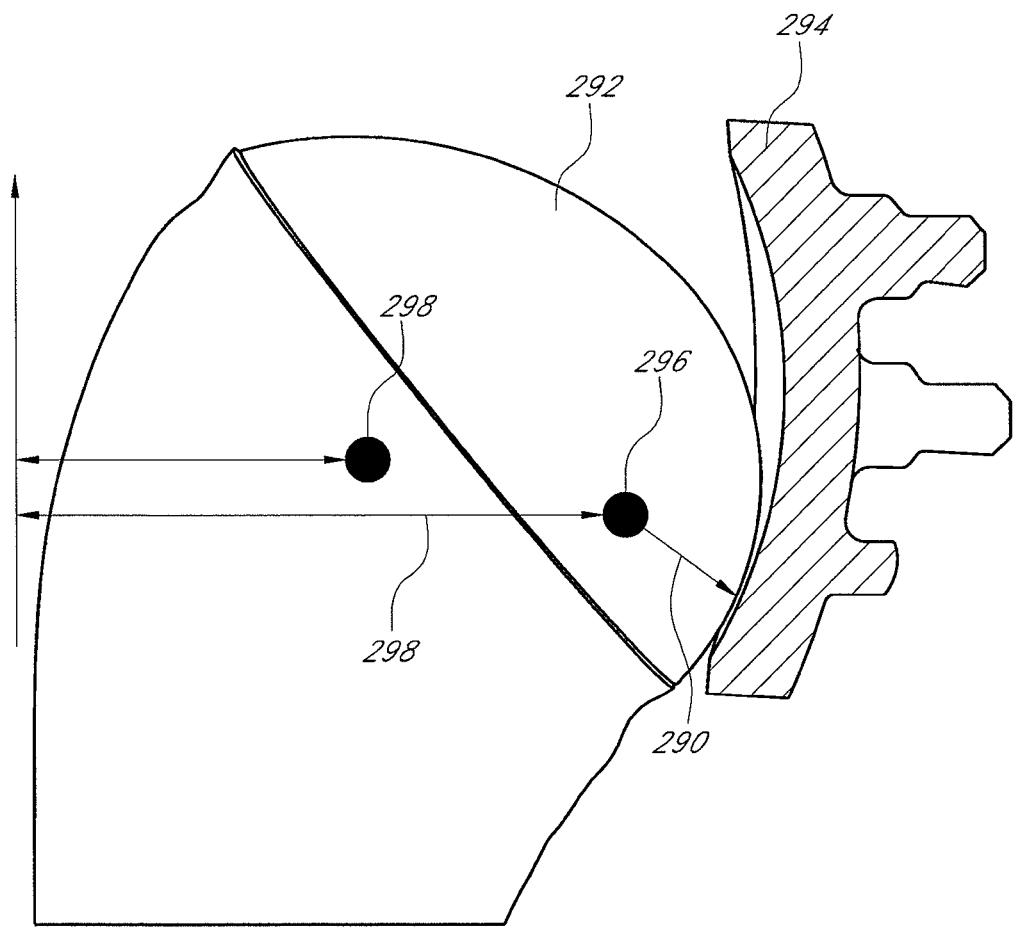
FIG. 31 shows how a non-spherical head can increase moment, according to another embodiment.

Moment on a joint can be increased either by increasing the muscle force that is applied to the joint, or by increasing the moment arm. As disclosed herein, embodiments of the non-spherical articulating surface can be used on either the humeral head or glenosphere to increase the moment in areas where the muscles can not apply enough force to flex the joint. For example, as shown in FIG. 31, a tighter radius of curvature 290 could be used locally where head 292 would contact bearing 294 in a neutral position to increase the moment during initial elevation. In such an embodiment, the head 292 has a center of curvature 296 that enables a moment arm to be locally increased to encourage flexing instead of sliding of the joint. This is true especially when compared to the much less moment arm achieved for a center of curvature 298 corresponding to a spherical head. The same geometry creation methods, as described above with reference to FIGS. 23 and 25 for the humeral head and glenosphere, could also be used in this case. In this case, the radius of curvature of the curvature of the sagittal curve could be made tighter in the inferior and or superior quadrants to increase moment at both extremes of motion or only in the inferior quadrant to increase motion accordingly.

Figure 32:
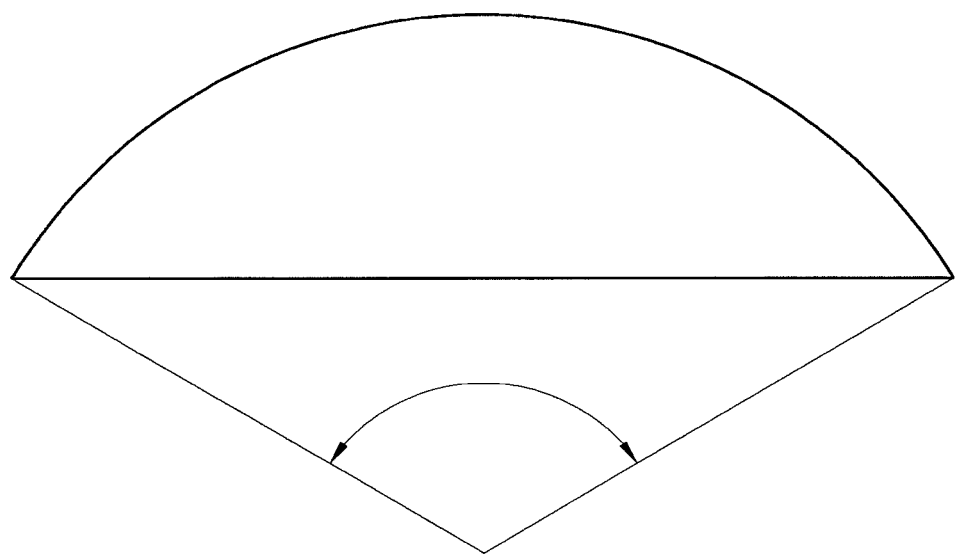
FIG. 32 shows a standard humeral head arc of motion.
Figure 33:
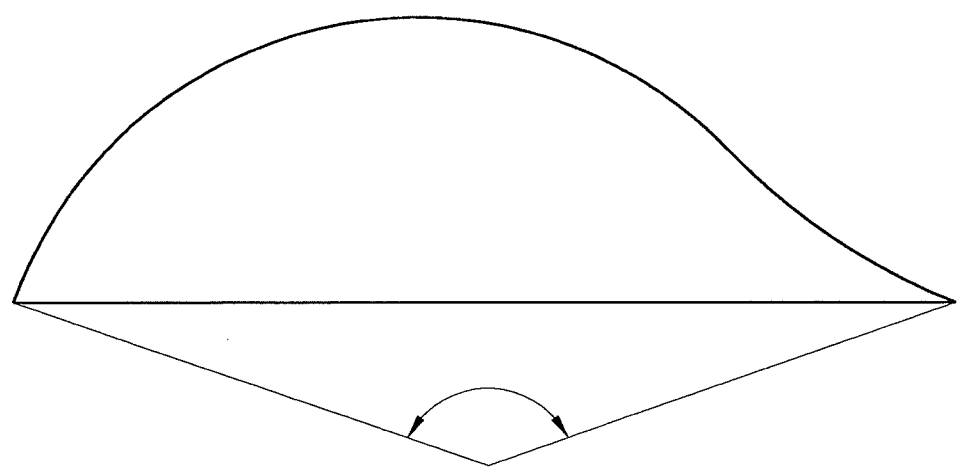
FIG. 33 shows a non-spherical, increased arc of motion, according to an embodiment.

Referring now to FIGS. 32-33, arc of motion is a measure of the angle to which a body can articulate before the point of contact corresponding to the angle of articulation reaches the edge of the functional surface. The arc of motion of a humeral head, for example, can limit flexion when it is too short to support the desired flexion angle. When this occurs, the joint simply can not flex enough without riding on the edge of the head, as shown in FIG. 17. As illustrated graphically in FIG. 32, an arc of motion for a spherical surface is defined mathematically as a product of the thickness and radius of curvature. However, as shown in FIG. 33, embodiments having a non-spherical surface as described herein can be used to increase this arc of motion independently of the thickness.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. An orthopedic device for ball and socket joint reconstruction, the orthopedic device comprising:
    a head component comprising a generally convex articulating surface, wherein the generally convex articulating surface includes at least three connecting radii defining a continuously varying curvature that is characterized by radii that gradually increase from a local minimum at a neutral position of the orthopedic device that is configured to be located at an area of contact on the convex articulating surface when an arm is in a neutral position, such that the head component is configured to define a locally increased moment arm at the neutral position; and
    a bearing component comprising a generally concave articulating surface.

2. The orthopedic device of claim 1, wherein the bearing component comprises a coupling mechanism that engages with a supportive substrate.

3. The orthopedic device of claim 2, wherein the coupling mechanism is selected from the group consisting of a tapered member, a screw, a locking mechanism, a peg, a keel, and a screw.

4. The orthopedic device of claim 1, wherein the bearing component is a glenoid resurfacing component, a reverse humeral bearing, or an acetabular bearing.

5. The orthopedic device of claim 1, wherein the head component is one of a humeral head, a femoral head, a reverse glenosphere, a humeral resurfacing component, and a femoral resurfacing component.

6. The orthopedic device of claim 1, wherein the head component is coupled to an intermediate substrate comprising a humeral stem, a femoral stem, a glenosphere base plate or a reverse humeral stem.

7. The orthopedic device of claim 1, comprising a fixation mechanism coupled to the bearing component, wherein the fixation mechanism comprises at least one of a glenoid peg, a locking mechanism for a reverse humeral stem, and a locking mechanism for an acetabular cup.

8. The orthopedic device of claim 1, wherein at least one of the generally convex articulating surface and the generally concave articulating surface comprises at least two continuously varying curvatures.

9. The orthopedic device of claim 1, wherein at least one of the generally convex articulating surface and the generally concave articulating surface comprises at least three curves having different radii of curvature corresponding to a central and a peripheral radii of the respective component.

10. The orthopedic device of claim 1, wherein at least one of the generally convex articulating surface and the generally concave articulating surface comprises at least two curves having different radii of curvature corresponding to an inferior and a superior radii of the respective component.

11. The orthopedic device of claim 1, wherein at least one of the generally convex articulating surface and the generally concave articulating surface comprises at least two curves having different radii of curvature corresponding to an anterior and a posterior radii of the respective component.

12. The orthopedic device of claim 1, wherein at least one of the generally convex articulating surface and the generally concave articulating surface comprises at least one curve swept along and normal to a second curve.

13. The orthopedic device of claim 1, wherein at least one of the generally convex articulating surface and the generally concave articulating surface comprises a first curve swept along and normal to a second curve, and gradually blended into the second curve.

14. The orthopedic device of claim 1, wherein at least one of the generally convex articulating surface and the generally concave articulating surface comprises at least two curves including a first curve swept along a second curve such that the first and second curves are blended together.

15. The orthopedic device of claim 1, wherein at least one of the generally convex articulating surface and the generally concave articulating surface comprises a configuration that locally varies at least one of constraint level, soft tissue tension, moment or arc of motion of a subject's joint.

16. An orthopedic device for joint reconstruction, the device comprising:
a head component comprising a generally convex articulating surface, wherein the generally convex articulating surface includes a non-spherical surface configuration including at least three connecting radii defining a continuously varying curvature that is characterized by radii that gradually increase from a local minimum at a neutral position of the orthopedic device, where the non-spherical surface configuration locally controls at least one of a constraint level, soft tissue tension, moment and arc of motion of a subject's joint; and
a bearing component comprising a generally concave articulating surface.

17. The orthopedic device of claim 16, wherein the non-spherical surface increases the moment of the subject's joint by increasing a thickness of the head component or the bearing component.

18. The orthopedic device of claim 16, wherein the non-spherical surface increases the moment of the subject's joint by decreasing the radius of curvature moving toward the local minimum.

19. The orthopedic device of claim 16, wherein the non-spherical surface increases or decreases the constraint level by varying the conformity with a mating body of the subject's joint.

20. The orthopedic device of claim 16, wherein the non-spherical surface increases or decreases the constraint level by increasing or decreasing a contact normal reaction force angle.

21. The orthopedic device of claim 16, wherein the non-spherical surface increases or decreases the soft tissue tension by increasing a thickness of the head component or the bearing component.

* * * * *